United States Patent [19]
Mathiesen et al.

[11] Patent Number: 6,110,161
[45] Date of Patent: Aug. 29, 2000

[54] METHOD FOR INTRODUCING PHARMACEUTICAL DRUGS AND NUCLEIC ACIDS INTO SKELETAL MUSCLE

[75] Inventors: Iacob Mathiesen, Oslo; Terje Lomo, Nesodden, both of Norway

[73] Assignee: Electrofect AS, Oslo, Norway

[21] Appl. No.: 09/055,084

[22] Filed: Apr. 3, 1998

Related U.S. Application Data

[60] Provisional application No. 60/042,594, Apr. 3, 1997.

[51] Int. Cl.[7] .................................................. A61N 1/30
[52] U.S. Cl. ............................................. 604/500; 604/20
[58] Field of Search .............................. 604/20–21, 500; 435/173.6

[56] References Cited

U.S. PATENT DOCUMENTS

| | | | |
|---|---|---|---|
| 5,273,525 | 12/1993 | Hofmann | 604/21 |
| 5,304,120 | 4/1994 | Crandell et al. | 604/52 |
| 5,318,514 | 6/1994 | Hofmann | 604/20 |
| 5,389,069 | 2/1995 | Weaver | 604/21 |
| 5,468,223 | 11/1995 | Mir | 604/51 |
| 5,501,662 | 3/1996 | Hofmann | 604/20 |
| 5,702,359 | 12/1997 | Hofmann et al. | 604/20 |
| 5,810,726 | 9/1998 | Hofmann | 604/20 |
| 5,944,710 | 8/1999 | Dev et al. | 604/500 |
| 5,964,726 | 10/1999 | Korenstein et al. | 604/20 |
| 5,993,434 | 10/1999 | Dev et al. | 604/501 |

FOREIGN PATENT DOCUMENTS

| | | | |
|---|---|---|---|
| WO95/23211 | 8/1995 | WIPO . | |
| WO 99/01157 | 1/1999 | WIPO | A61K 48/00 |

OTHER PUBLICATIONS

Bhatt, D., Gaylor, D. & Lee, R., (1990); "Rhabdomyolysis Due to Pulsed Electric Fields"; *Plastic and Reconstructive Surgery* vol. 86, No. 1, pp.1–11.

Block, T. A., Aarsvold, J. N., Matthews, K. L., Mintzer, R. A., River, L. P., Schellpfeffer, M. C., Wollmann, R. L., Tripathi, S., Chen, C.–T. & Lee, R. C.(1995); "Nonthermally Mediated Muscle Injury and Necrosis in Electrical Trauma"; *Journal of Burn Care & Rehabilitation*, vol. 16, No. 6, pp. 581–588.

Collas, P., Husebye, H. & Alestrom, P. (1996); "The Nuclear Localization Sequence of the SV40 T Antigen Promotes Transgene Uptake and Expression in Zebrafish Embryo Nuclei"; *Transgenic Research* vol. 5, pp. 451–458.

Davis, H. L., Whalen, R. G. & Demeneix, B. A. (1993); "Direct Gene Transfer into Skeletal Muscle In Vivo: Factors Affecting Efficiency of Transfer and Stability of Expression"; *Human Gene Therapy* vol. 4, pp. 151–159.

Heller, R., Jaroszeski, M., Atkin, A., Moradpour, D., Gilbert, R., Wands, J. & Nicolau, C. (1996); "In Vivo Gene Electroinjection and Expression in Rat Liver", *FEBS Letter* vol. 389, pp. 225–228.

(List continued on next page.)

*Primary Examiner*—Mark Bockelman
*Attorney, Agent, or Firm*—Madson & Metcalf

[57] ABSTRACT

A method is disclosed for delivering molecules such as pharmaceutical drugs and nucleic acids into skeletal muscle in vivo. The pharmaceutical drug or nucleic acid is first injected into the muscle at one or multiple sites. Immediately, or shortly after, injection, electrodes are placed flanking the injection site and a specific amount of electrical current is passed through the muscle. The electrical current makes the muscle permeable, thus allowing the pharmaceutical drug or nucleic acid to enter the cell. The efficiency of transfer permits robust immune responses using DNA vaccines and produces sufficient secreted proteins for systemic biological activity to be observed.

22 Claims, 21 Drawing Sheets

(8 of 21 Drawing Sheet(s) Filed in Color)

OTHER PUBLICATIONS

Hofmann, G. A. (1989); "Cells in Electric Fields"; In *Electroporation and Electrofusion in Cell Biology*, ed. Neuman, E., Sowers, A. E. & Jordan, C. A., pp. 389–407; Plenum Publishing Corporation.

Lee, R. C., Canaday, D. J. & Hammer, S. M. (1993); "Transient and Stable Ionic Permeabilization of Isolated Skeletal Muscle Cells After Electrical Shock"; *Journal of Burn Care & Rehabilitation* vol. 14, No. 5, pp. 528–540.

Lee, R. C., River, L. P., Pan, F.–S., Ji, L. & Wollmann, R. L. (1992); "Surfactant–Induced Sealing of Electropermeabilized Skeletal Muscle Membranes In Vivo"; *Proc. Natl. Acad. Sci. USA* vol. 89, pp. 4524–4528.

Manthorpe, M., Comfert–Jensen, F., Hartikka, J., Felgner, J., Rundell, A., Margalith, M. & Dwarki, V. (1993); "Gene Therapy by Intramuscular Injection of Plasmid DNA: Studies on Firefly Luciferase Gene Expression in Mice"; *Human Gene Therapy* vol. 4, pp. 419–431.

Miklavcic, D., Beravs, K., Semrov, D., Cemazar, M., Demsar, F. & Sersa, G. (1998); "The Importance of Electric Field Distribution for Effective In Vivo Electroporation of Tissues"; *Biophysical Journal* vol. 74, pp. 2152–2158.

Nishi, T., Yoshizato, K., Yamashiro, S., Takeshima, H., Sato, K., Hamada, K., Kitamura, I., Yoshimura, T., Saya, H., Kuratsu, J. & Ushio, Y. (1996); "High–Efficiency In Vivo Gene Transfer Using Intraarterial Plasmid DNA Injection Following In Vivo Electroporation"; *Cancer Research* vol. 56, pp. 1050–1055.

Potter, H. (1988); "Electroporation in Biology: Methods, Applications, and Instrumentation"[Review]; *Analytical Biochemistry* vol. 174, pp. 361–373.

Prausnitz, M. R., Bose, V. G., Langer, R. & Weaver, J. C. (1993); "Electroporation of Mammalian Skin: A Mechanism to Enhance Transdermal Drug Delivery"; *Proc. Natl. Acad. Sci. USA* vol. 90, pp. 10504–10508.

Rols, M.–P. & Teissie, J. (1990); "Electropermeabilization of Mammalian Cells: Quantitative Analysis of the Phenomenon"; *Biophysical Journal* vol. 58, pp. 1089–1098.

Rols, M.–P., Delteil, C., Golzio, M., Dumond, P., Cros, S. & Teissie, J. (1998); "In Vivo Electrically Mediated Protein and Gene Transfer in Murine Melanoma"; *Nature Biotechnology* vol. 16, pp. 168–171.

Tekle, E., Astumian, R. D. & Chock, P. B. (1991); "Electroporation by using Bipolar Oscillating Electric Field: An Improved Method for DNA Transfection of NIH 3T3 Cells"; *Proc. Natl. Acad. Sci. USA* vol. 88, pp. 4230–4234.

Wolf, H., Rols, M. P., Boldt, E., Neumann, E. & Teissie, J. (1994); "Control by Pulse Parameters of Electric Field–Mediated Gene Transfer in Mammalian Cells"; *Biophysical Journal* vol. 66, pp. 524–531.

Wolff, J. A., Ludtke, J. J. Acsadi, G., Williams, P. & Jani, A. (1992); "Long–Term Persistence of Plasmid DNA and Foreign Gene Expression in Mouse Muscle"; *Human Molecular Genetics* vol. 1, No. 6, pp. 363–369.

Wolff, J. A., Williams, P., Acsadi, G., Jiao, S., Jani, A. & Chong, W. (1991); "Conditions Affecting Direct Gene Transfer into Rodent Muscle in Vivo"; *Biotechniques* vol. 11, pp. 474–485.

EDL, fast    SOL, slow a All muscles are denervated

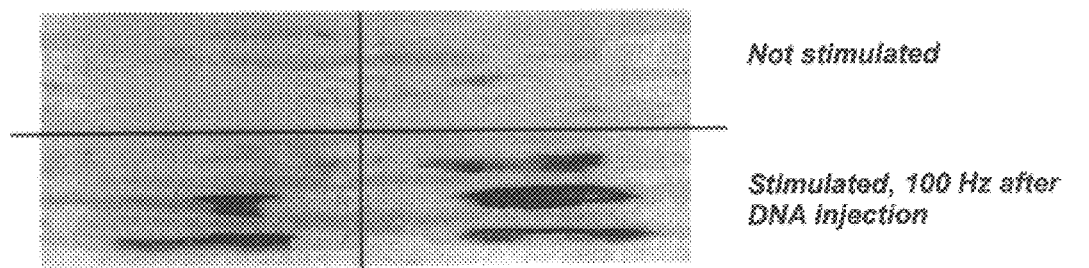

Not stimulated

Stimulated, 100 Hz after DNA injection b All muscles are stimulated directly with 100 Hz after DNA injection

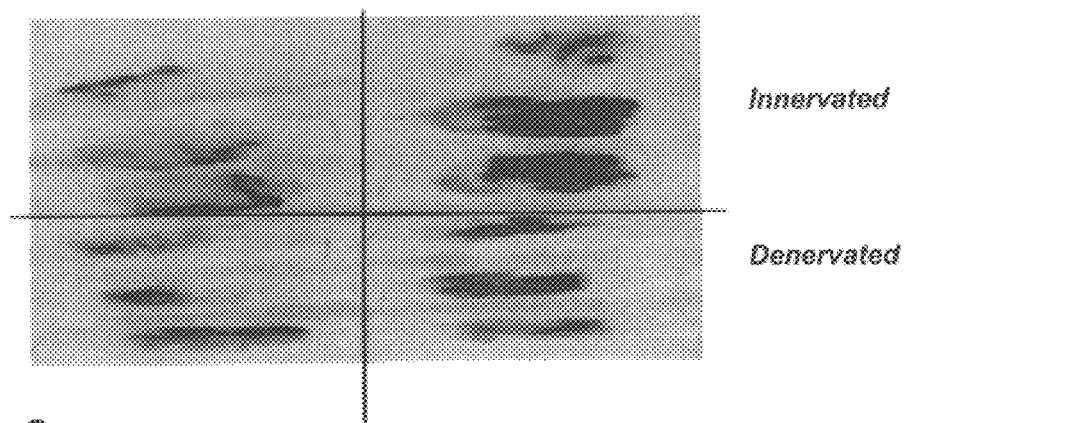

Innervated

Denervated c All muscles have been active

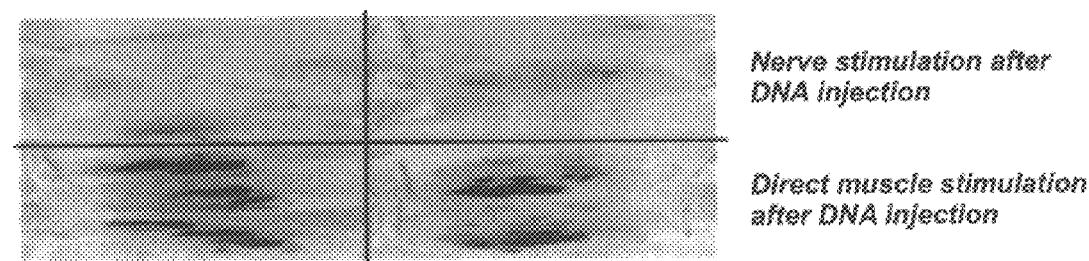

Nerve stimulation after DNA injection

Direct muscle stimulation after DNA injection d All muscles have been stimulated directly with 100 Hz

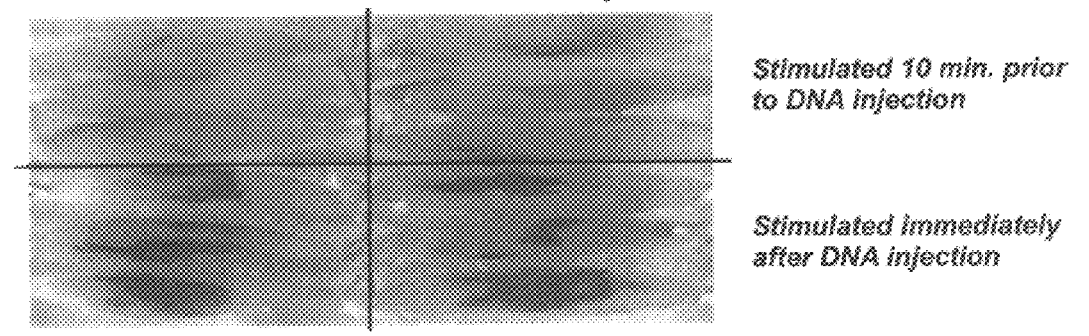

Stimulated 10 min. prior to DNA injection

Stimulated immediately after DNA injection

Fig. 3

METHOD FOR INTRODUCING PHARMACEUTICAL DRUGS AND NUCLEIC ACIDS INTO SKELETAL MUSCLE

1. RELATED APPLICATIONS

This application is related to and claims the benefit of U.S. Provisional Application Serial No. 60/042,594 of Iacob Mathiesen and Terje Lomo filed Apr. 3, 1997 and entitled "Apparatus and Method for Introducing Pharmaceutical Drugs and Genetic Material Into Skeletal Muscle," which is incorporated herein by this reference.

2. FIELD OF THE INVENTION

The present invention is related to a method for making skeletal muscle semipermeable to pharmaceutical drugs and nucleic acids. More specifically, skeletal muscle is made semipermeable by electrically stimulating the muscle at low field strengths following pharmaceutical drugs and nucleic acids injection.

3. TECHNICAL BACKGROUND

Scientists are continually discovering genes which are responsible for many human diseases, such as genes responsible for some forms of breast cancer, colon cancer, muscular dystrophy and cystic fibrosis. In addition, scientists are continually discovering genes that code for bacterial and viral antigens (e.g., viral capsid proteins). Despite these new discoveries, a major obstacle facing the medical profession is how to safely deliver effective quantities of these agents to patients to treat disease or for genetic immunization.

Currently, most pharmaceutical agents are taken orally or intravenously. Oral and intravenous drug and gene delivery methods, however, have several shortcomings. First, a large percent of orally or intravenously delivered drugs are degraded by the body before arriving at the target organ or cells. Acids and enzymes in the stomach and intestine, for example, can break down many pharmaceutical drugs. Similarly, genes would be rapidly destroyed by proteins found in the blood and liver which break down DNA. Additionally, intravenously delivered drugs and genes are often sequestered by the liver or immune system before arriving at the diseased organ or cells. Second, oral and intravenous drug and gene delivery is non-specific. That is, the drug or gene is delivered to both target and non-target cells.

Skeletal muscle is a promising candidate for drug delivery, gene therapy and genetic immunization. First, skeletal muscle constitutes over 50% of a human's body mass, most of which is easily accessible compared to other tissues and organs of the body. Second, there are numerous inherited and acquired disorders, such as Duchenne muscular dystrophy (DMD), diabetes mellitus, hyperlipidaemia and cardiovascular disease which are good candidate disorders for drug and gene delivery into the muscle. Third, muscle is an ideal site for genetic immunization because it is easily accessible and proteins made in the muscle are secreted, thus eliciting an immune response. Finally, skeletal muscle cells are non-dividing. Therefore, skeletal muscle cells are capable of expressing a protein coded by a gene for a longer time period than would be expected of other cell types that are continually dividing. Because the protein is expressed for a longer time, fewer treatments would be necessary.

Currently, however, there is no non-viral method for effectively delivering pharmaceutical drugs and DNA into skeletal muscle in vivo. There are several methods known in the art for transferring pharmaceutical drugs and DNA into skeletal muscle, such as intramuscular injection of DNA. The clinical applicability of direct muscle injection, however, is limited mainly because of low transfection efficiency, typically less than 1% transfection efficiency. It has been demonstrated that the efficacy of transfection can be improved if DNA injections are done in regenerating muscle. Injection is induced three days before DNA injection with the drug Bivucain. While injection in regenerating muscles induced by Bivucain show higher efficiency, the method has limited applicability in humans because of the severe damage caused to the muscle.

From the foregoing, it will be appreciated that it would be an advancement in the art to provide a non-viral method of delivering pharmaceutical drugs and DNA only to diseased organs and cells. It would also be an advancement in the art to provide an electroporation method of delivering pharmaceutical drugs and DNA directly into skeletal muscle. It would be yet another advancement in the art if the electroporation method could deliver therapeutically effective quantities of pharmaceutical drugs and DNA into the skeletal muscle at multiple sites simultaneously. It would be a further advancement if the method permitted the delivery efficiencies to be regulated.

Such a method is disclosed herein.

4. BRIEF SUMMARY OF THE INVENTION

The present invention provides a method for delivering or transfecting pharmaceutical drugs and DNA into skeletal muscle. Without being bound by theory, the method is thought to be similar to electroporation. Electroporation works on the principle that cells act as an electrical capacitor generally unable to pass current. Subjecting cells to a high-voltage electric field, therefore, creates transient permeable structures or micropores in the cell membrane. These pores are large enough to allow pharmaceutical drugs, DNA and other polar compounds to gain access to the interior of the cell. With time, the pores in the cell membrane close and the cell once again becomes impermeable.

Conventional electroporation, however, employs high field strengths from 0.4 to several kV/cm. In contrast to conventional electroporation, the field strength used in the present invention ranges from about 25 V/cm to 250 V/cm. These lower field strengths are thought to cause less muscle damage without sacrificing, and indeed increasing, transfection efficiencies. Furthermore, using the method of the present invention, transfection efficiencies can be tightly regulated by altering such parameters as frequency, pulse duration and pulse number.

The increase in DNA transfection efficiency is observed only if the muscle is electrically stimulated immediately, or shortly after the DNA injection. Thus, the semipermeable quality of the tissue induced by the stimulation is reversible. Moreover, it is dependent on current through the muscle; activity induced through the nerve does not affect transfection efficiency.

Once transfected, the muscle cells are able to express the proteins coded by the nucleic acid. Therefore, the transfection method of the present invention can be used, for example, to transfect expression vectors for genetic immunization (i.e., DNA vaccines). In one embodiment, rabbits were transfected with a plasmid containing the cDNA for rat agrin. The transfected muscles produced and secreted agrin protein. Nineteen days post-transfection, rabbit serum contained significant antibodies against rat agrin.

In a second embodiment, mice and rats were transfected using the method of the present invention with one or more of three different eukaryotic expression vectors containing the coding sequences for DH-CNTF, an agonistic variant of human ciliary neurotrophic factor, AADH-CNTF, an antagonistic variant of human ciliary neurotrophic factor and sec-DH-CNTF, a secreted form of DH-CNTF. The muscles were either not electrically stimulated or stimulated immediately after DNA injection. Blood was collected at various time points and the antibody titers determined. In both rats and mice, electrical stimulation immediately after DNA injection led to approximately 5 to 10-fold higher antibody titers than simple DNA injection.

The transfection method of the present invention can also be used to systemically deliver proteins to treat diseases. In one preferred embodiment, a DNA plasmid harboring the erythropoietin (EPO) gene was injected into skeletal muscle and stimulated according to the method of the present invention. Controls were either not stimulated or transfected with a control vector not harboring the EPO gene. After 14 days, only the mice transfected with EPO according to the method of the present invention displayed an increased hematocrit indicating the transfected muscles were able to produce and secrete into the blood stream substantial amounts of EPO.

Non-nucleic acids may also be transfected by the method of the present invention. In one embodiment, rhodamin conjugated dextran was injected into the muscle followed by electrical stimulation. Three to five days later the muscles were frozen in liquid nitrogen and sectioned on a cryostat. Fluorescence was observed in cells injected and stimulated, indicating the rhodamin conjugated dextran was able to enter and remain in the muscle cells.

These and other objects and advantages of the present invention will become apparent upon reference to the accompanying drawings and graphs and upon reading the following detailed description and appended claims.

5. SUMMARY OF THE DRAWINGS

The file of this patent contains at least one drawing executed in color. Copies of this patent with color drawing (s) will be provided by the Patent and Trademark Office upon request and payment of the necessary fee.

A more particular description of the invention briefly described above will be rendered by reference to the appended drawings and graphs. These drawings and graphs only provide information concerning typical embodiments of the invention and are not therefore to be considered limiting of its scope.

FIG. 1—graphically illustrates the method of delivering pharmaceutical drugs and DNA into skeletal muscle of the present invention.

FIG. 2—is a graphical illustration of an electrical stimulation delivered according to the method of the present invention.

FIG. 3—illustrates whole mounts of muscles which have been injected with 50 µl of RSV-Lac Z Plasmid DNA solution at a concentration of 1 µg/µl. Muscles in 3a and 3b were taken out 15 days after DNA injection. Muscles in 3c and 3d were taken out 7 days after DNA injection. All muscles are pairs from the same rat.

FIG. 4—pictures a whole muscle and a 1 mm slice of a transfected muscle. Dark stain indicates o-nitrophenyl-b-D-galactopyranoside (ONPG) that has been catalyzed by β-galactosidase in the muscle to yield a dark precipitate. Arrows illustrate muscle fibers that were successfully transfected using the method of the present invention.

FIG. 5—includes mean number of transfected fibers from each group of skeletal muscles shown in FIG. 3.

FIG. 6—is a bar graph illustrating mean transfected fibers of muscles from several different experiments and several different batches of DNA grouped together. In columns marked SOL S and EDL S the muscles (16 in each group) have been stimulated directly after the injection of DNA. In columns marked SOL NS and EDL NS the muscles (10 in each group) have been stimulated by the nerve, not stimulated at all or stimulated directly 10 minutes before the DNA injection.

FIG. 7—is a graph illustrating the number of skeletal muscle fibers transfected versus the log of the stimulation frequency. The duration of the stimulation train was kept constant at 1 second.

FIG. 8—is a photograph of transfected muscles from which data in FIG. 7 were generated.

FIG. 9—illustrates the results achieved when whole mounts of muscles were transfected according to the method of the present invention using two different electrodes.

FIG. 10—is a graph illustrating the number of skeletal muscle fibers transfected with increasing frequency compared to increasing pulse number.

FIG. 11—is a graph illustration of the number of skeletal muscle fibers transfected versus the number of pulses at constant frequency.

FIG. 12—is a graph illustrating mean luciferace activity versus the number of pulses.

FIG. 13—is a graph illustrating the voltage dependency of the stimulation method of the present invention.

Figure 14:
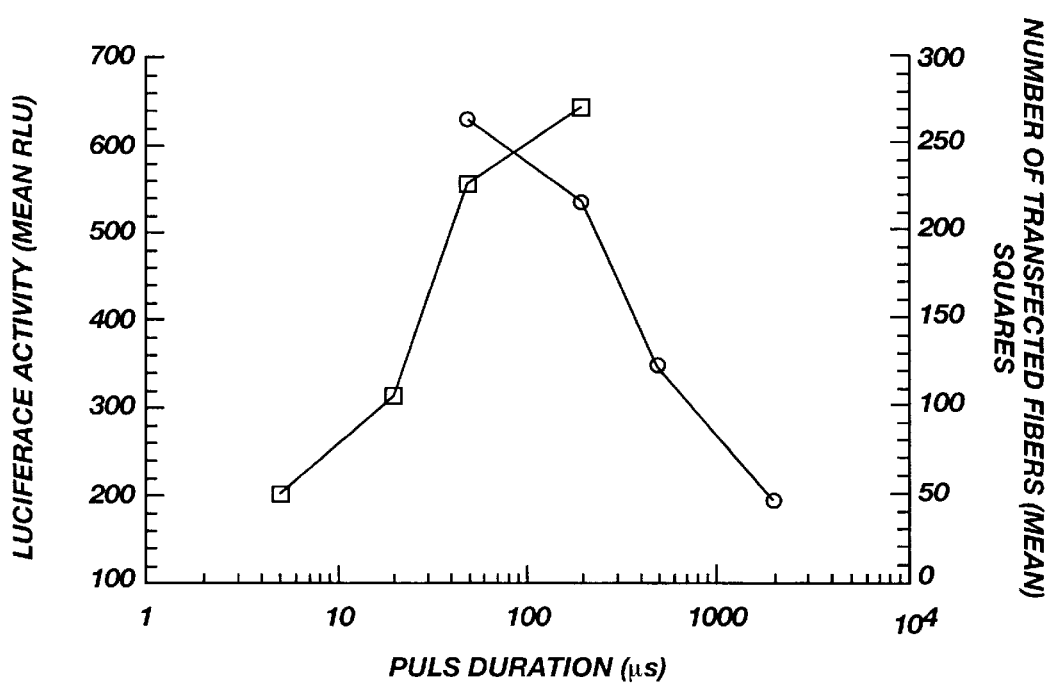

FIG. 14—is a graph illustrating the effect of pulse duration on the transfection efficiency.

Figure 15:
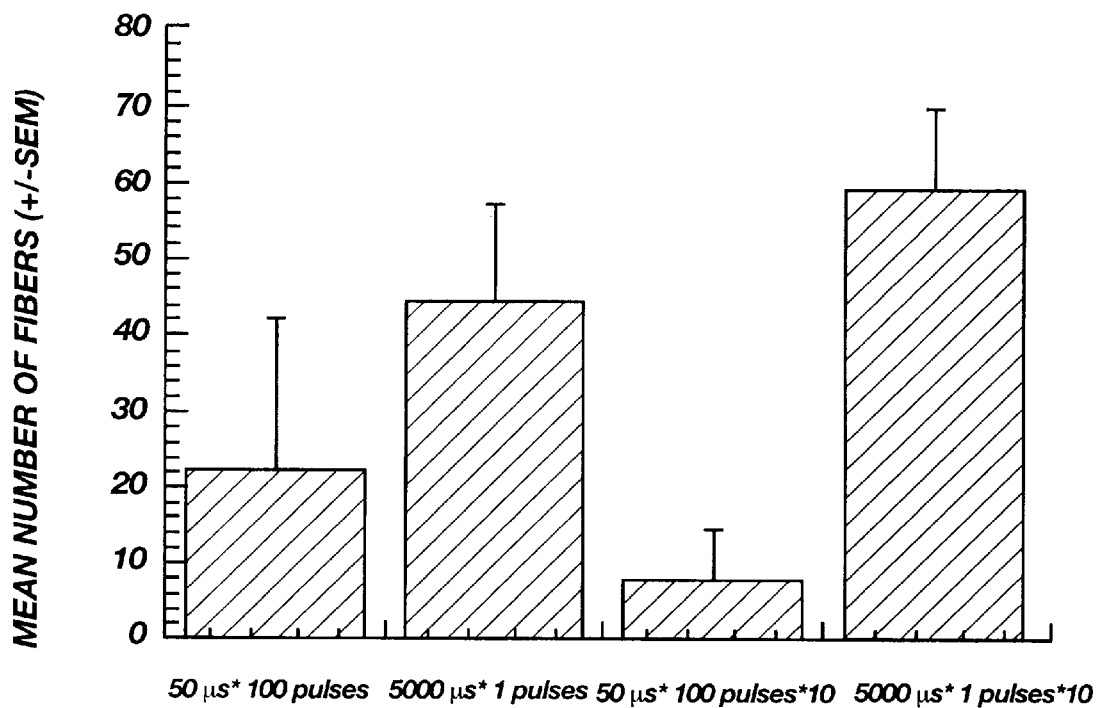

FIG. 15—is a bar graph illustrating a comparison of transfection efficiencies for varying pulse durations and pulse numbers.

Figure 16:
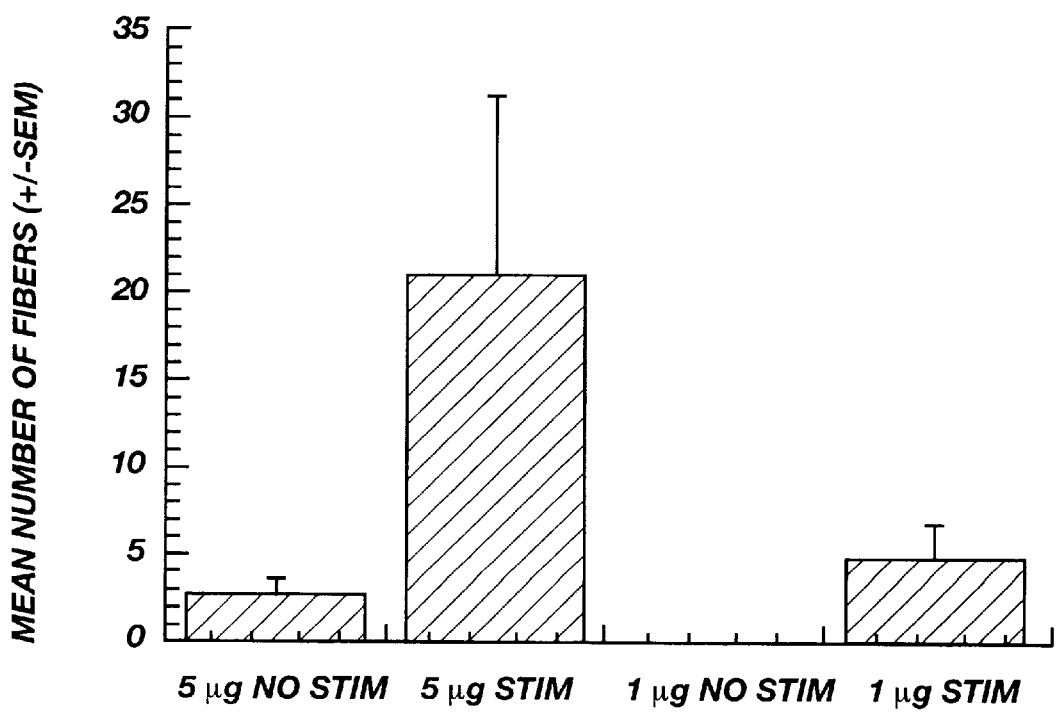

FIG. 16—is a bar graph illustrating the effect of DNA concentration on transfection efficiency.

FIG. 17—is a photograph of transfected muscles illustrating damage caused by stimulation and regeneration of the muscle after a short period of time.

Figure 17A:

FIG. 17a illustrates an injected muscle that was not stimulated.

Figure 17B:

FIG. 17b illustrates muscle damage following muscle stimulation.

Figure 17C:

FIG. 17c illustrates muscle stimulated under harsher stimulation conditions.

Figure 17D:
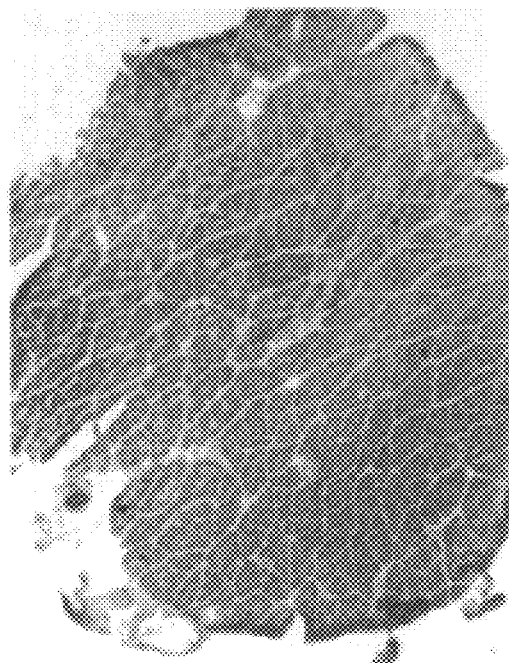

FIG. 17d illustrates that muscles stimulated under the conditions of muscles in 17c are completely regenerated and repaired after 14 days.

Figure 17E:

FIG. 17e illustrates muscles transfected with green fluorescent protein (GFP).

Figure 17F:
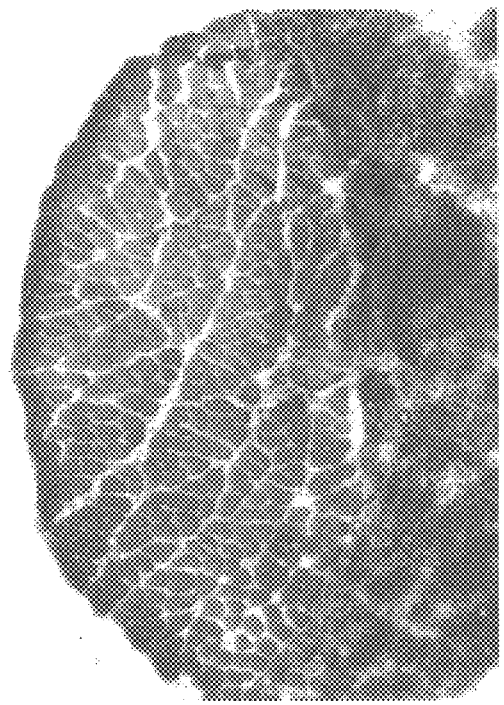

FIG. 17f illustrates that transfected fibers can bee seen in the vicinity of the damaged area.

FIGS. 18a–d are a photograph of cells stained with anti-agrin polyclonal antibodies derived from a rabbit genetically immunized with an expression vector coding for rat agrin using the stimulation technique of the present invention.

Figure 19:
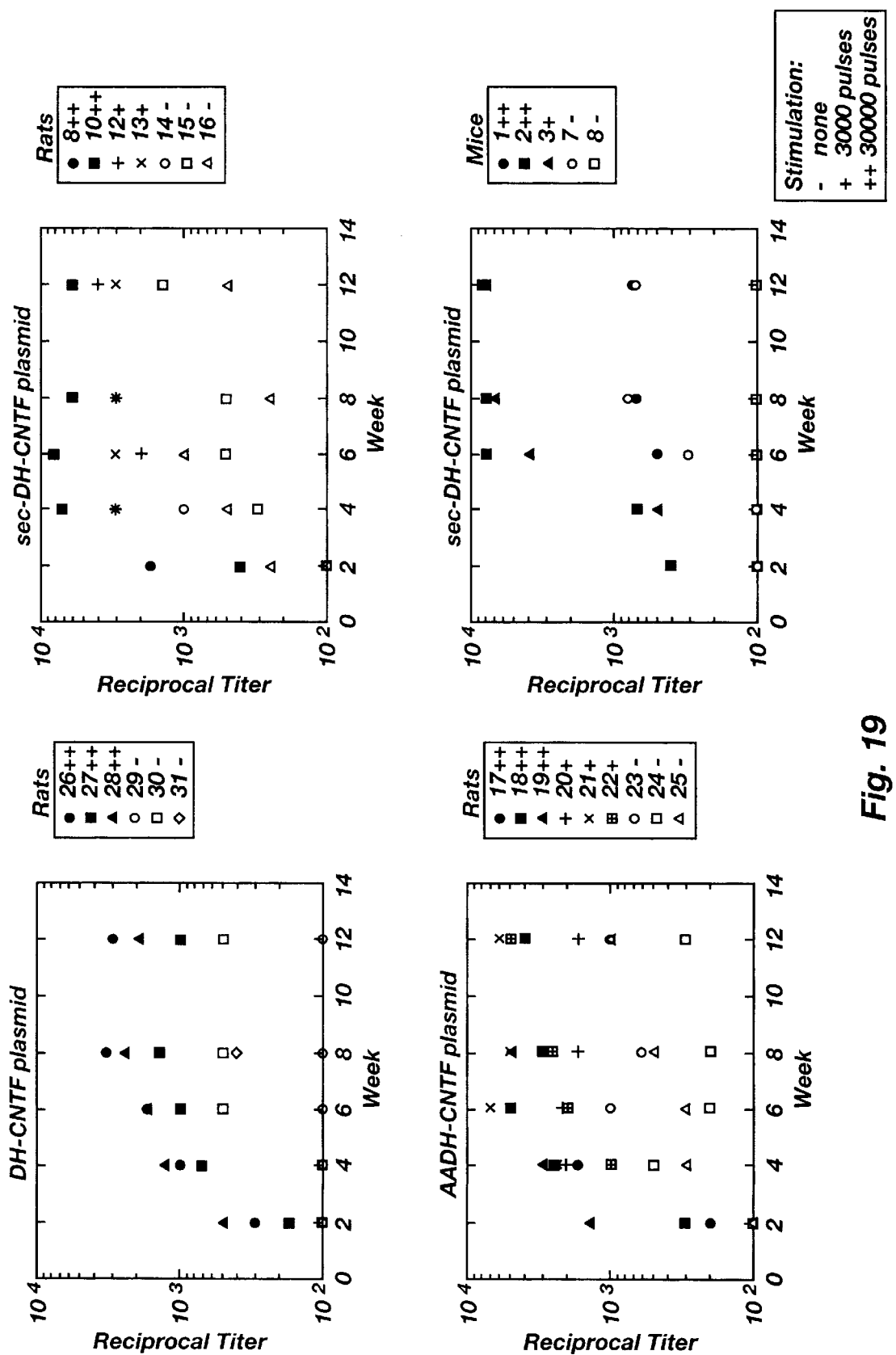

FIG. 19—are graphs illustrating improved genetic immunization of mice and rats using the stimulation technique of the present invention versus naked DNA injection.

Figure 20:
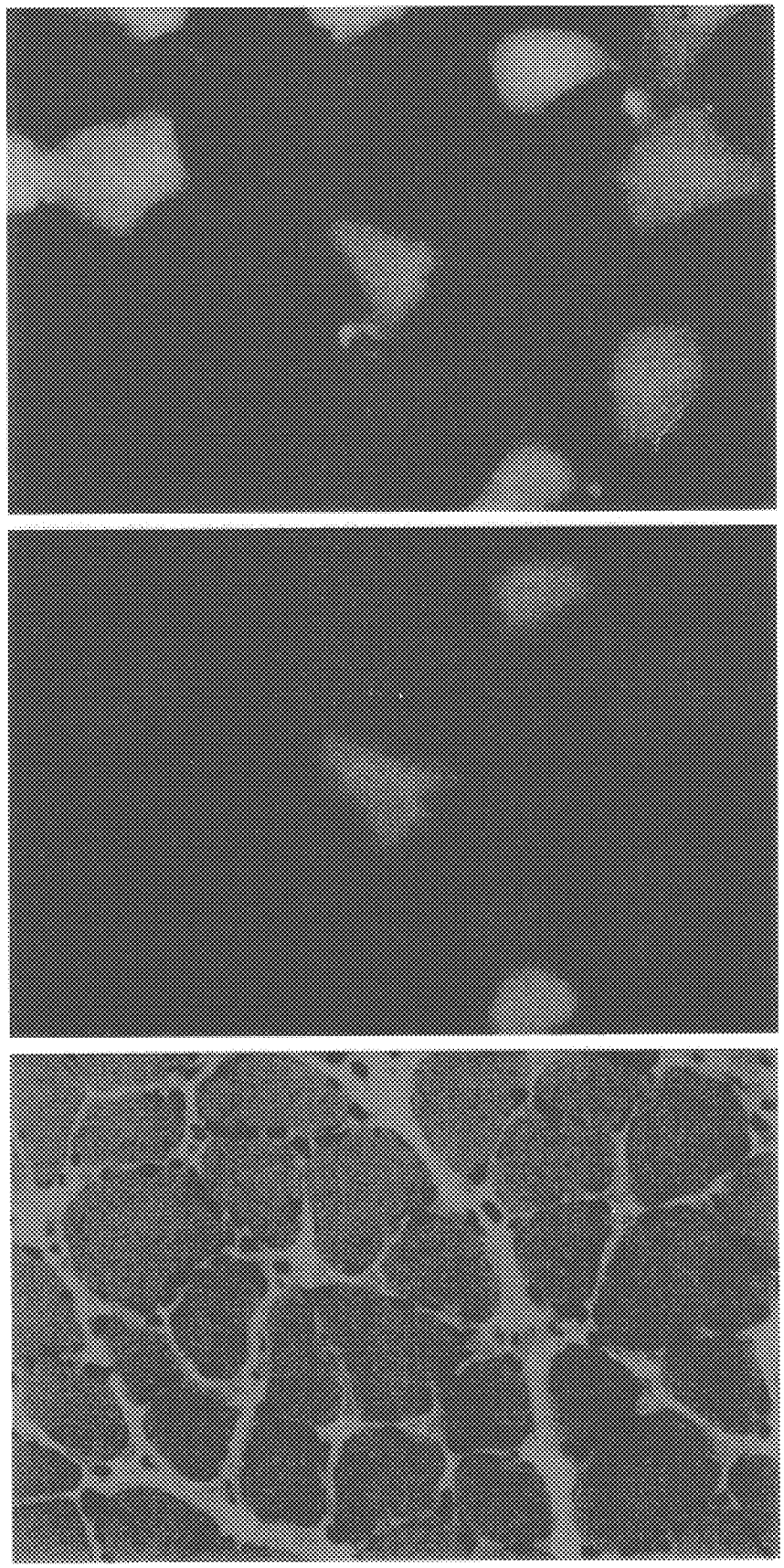

FIG. 20—is a photograph of muscles transfected with rhodamine-conjugated dextran and green fluorescent protein. Top: rhodamin fluorescence from rhodamine conjugated dextran. Middle: The same section as above but with filters revealing GFP fluorescence. Bottom: hematoxilin and eosin staining of a neighboring section.

6. DETAILED DESCRIPTION OF THE INVENTION

The present invention is directed to a novel method for increasing the permeability of skeletal muscle tissue, thus allowing pharmaceutical drugs and nucleic acids to enter or transfect the cells. The method of the present invention passes a predetermined amount of electrical current through the skeletal muscle tissue. Unlike previously described electroporation methods, however, the parameters of the method of the present invention are unique, particularly with respect to the low field strength used and the amount of damage that occurs. Other parameters such as the number of trains, frequency, pulse number and pulse duration can be varied in order to regulate the amount of pharmaceutical drug or nucleic acid delivered.

Figure 1:
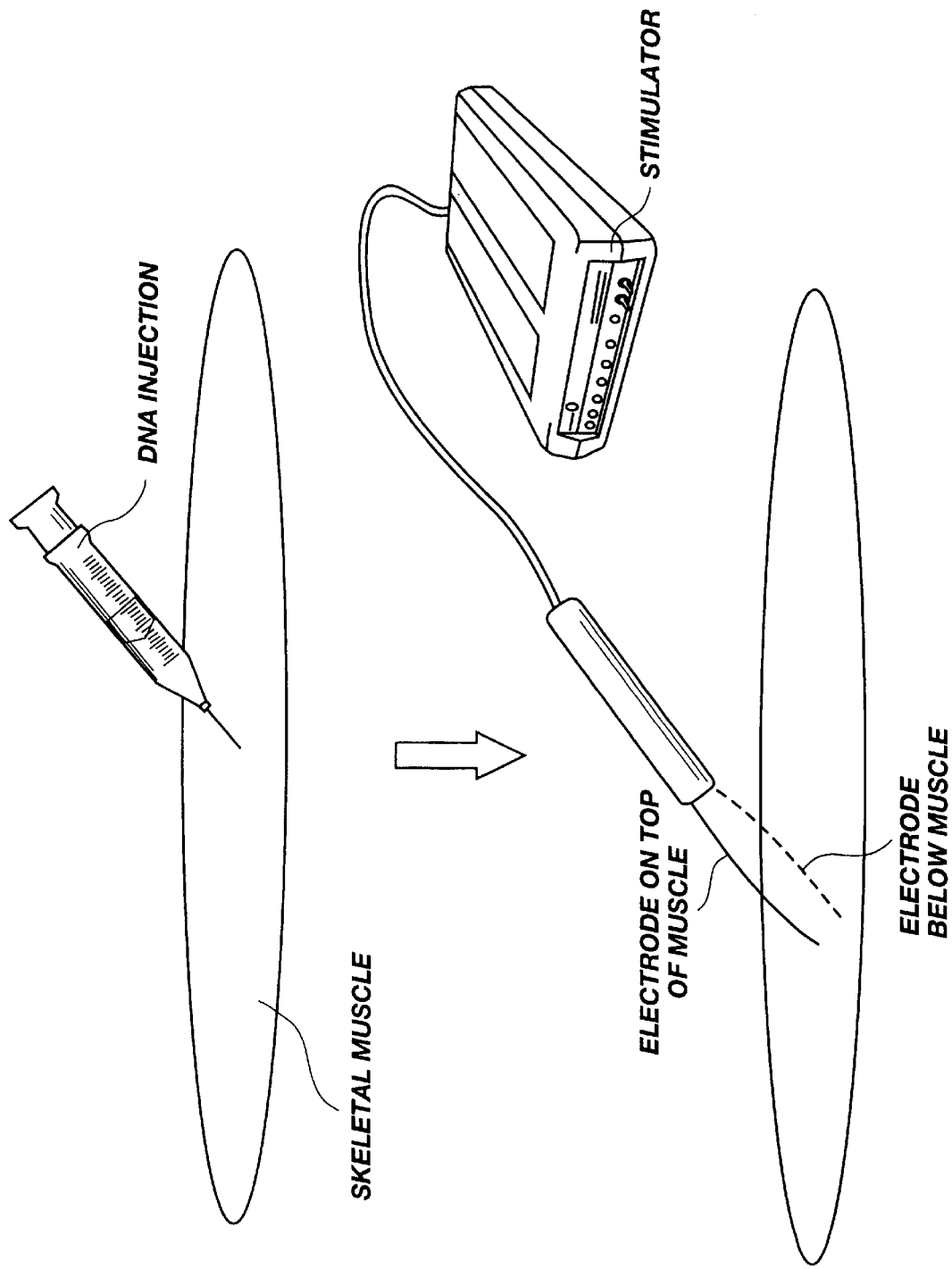

As illustrated in FIG. 1, generally, skeletal muscle is exposed and a predetermined amount of a molecule is injected into the muscle. In one embodiment the DNA is dissolved in 0.9% sodium chloride (NaCl). The exact solvent, however, is not critical to the invention. For example, it is well known in the art that other solvents such as sucrose are capable of increasing DNA uptake in skeletal muscle. Other substances may also be co-transfected with the molecule of interest for a variety of beneficial reasons. For example, P188 (Lee, et al. PNAS., 4524–8, 10, 89 (1992)), which is known to seal electropermeabilized membranes, may beneficially affect transfection efficiencies by increasing the survival rate of transfected fibers.

With continued reference to FIG. 1, electrodes are placed on the muscle, about 1–4 mm apart, near the area where the molecule was injected. The exact position or design of the electrodes is not critical so long as current is permitted to pass through the muscle fibers perpendicular to their direction in the area of the injected molecule.

Figure 2:
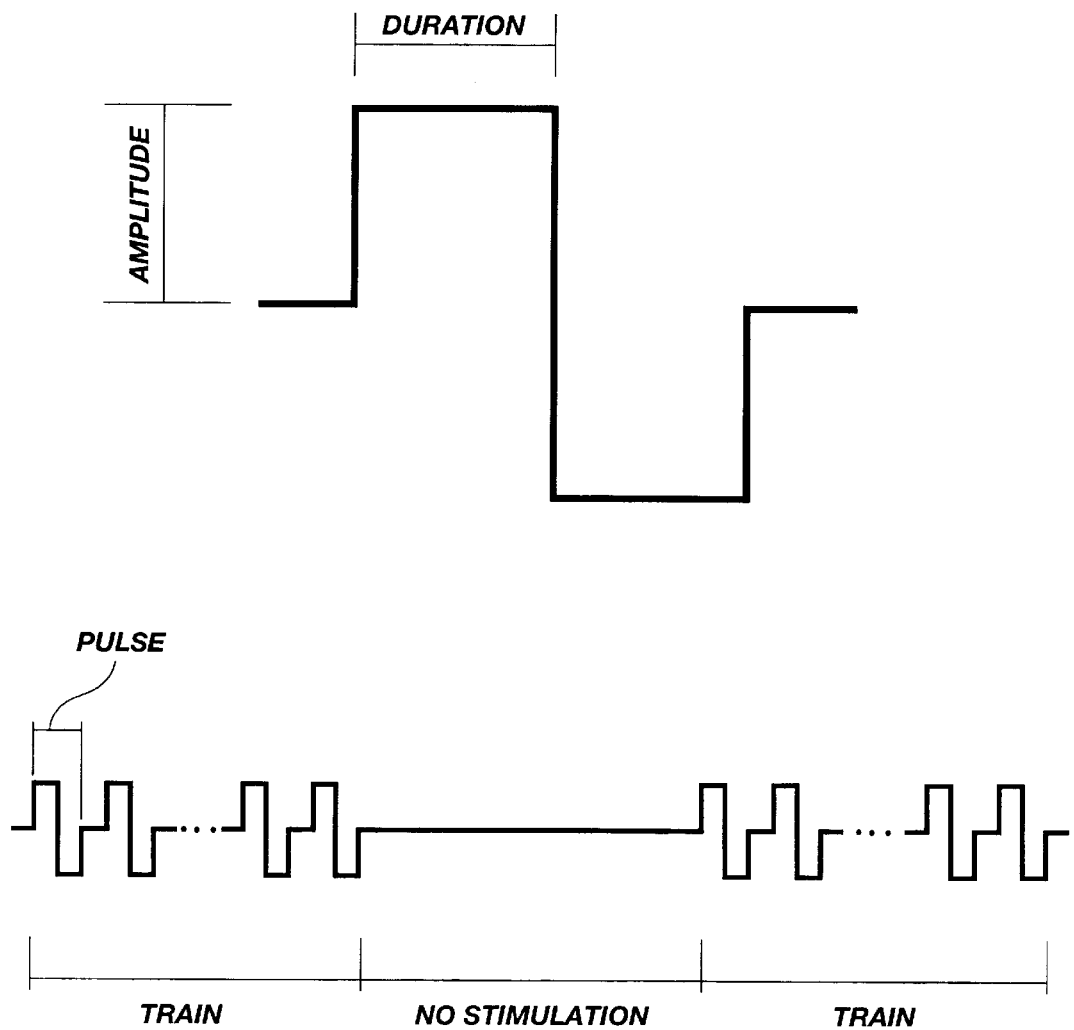

Once the electrodes are in position, the muscle is electroporated or stimulated. As illustrated in FIG. 2, the stimulation is delivered as a square bipolar pulse having a predetermined amplitude and duration. In order to optimize the transfection efficiencies, these parameters have been widely varied and transfection efficiencies compared. For example, the voltages have ranged from approximately 0 to 50 volts; the pulse durations have ranged from 5 $\mu$s to 5 ms; the number of pulses have ranged from a single pulse to 30,000 pulses; and the pulse frequency within trains have ranged from 0.5 Hz to 1000 Hz.

The conclusion from these results is that so long as the field strength is above about 50 V/cm, the other parameters may be varied depending on the experimental conditions desired. While no upper limit was detected, effective transfection efficiencies were observed with much higher field strengths. The field strength of the stimulation can be calculated using the formula:

$$E=V/(2r \ln (D/r)),$$

which gives the electric field between wires if D>>r. In the formula, V=voltage=10 V, D=distance between wire centers=0.1–0.4 cm, r=diameter of electrode=0.06 cm. See Hofmann, G. A. Cells in electric fields. In E. Neumann, A. E. Sowers, & C. A. Jordan (Eds.), Electroporation and electrofusion in cell biology (pp. 389–407). Plenum Publishing Corporation (1989). At 10 volts, the field strength is between 163 V/cm–43 V/cm (from 0.1 to 0.4 cm between electrodes, respectively). Because D is not much greater than r, it may be more appropriate to use the formula for electric fields between large parallel plates:

$$E=V/D$$

This gives a similar field strength of between 100 V/cm–25 V/cm (from 0.1–0.4 cm between electrodes, respectively). It will be appreciated that the field strength, as well as other parameters, are affected by the tissue being transfected, and thus optimal conditions may vary. Using the parameters given in the present invention, however, optimal parameters can be easily obtained by one skilled in the art.

As illustrated in FIGS. 3 and 5–8, the method of the present invention dramatically increases the efficiency of drug and DNA delivery into skeletal muscle. In one embodiment, rat soleus or EDL muscles were injected with DNA plasmid containing the $\beta$-galactosidase gene (lac Z). The $\beta$-galactosidase gene yields a protein capable of converting a colorless substrate into a blue substrate that can be visually analyzed or measured spectrophotometrically. FIG. 3 depicts representative soleus and EDL muscles that have been transfected with $\beta$-galactosidase gene using various stimulation parameters.

FIG. 3a illustrates the improved DNA delivery efficiency of soleus and EDL muscles that have been transfected according to the method of the present invention. Soleus and EDL muscles (n=3) were first denervated by transecting the sciatic nerve. This was done to eliminate any influence of nerve-induced activity that arguably could contribute to the increased transfection efficiency observed. Three days post-denervation, the muscles were injected with the $\beta$-galactosidase gene as described above. After the DNA injection, the muscles were either untreated or, immediately after the DNA injection, the muscles were stimulated according to the method of the present invention.

Figure 4:
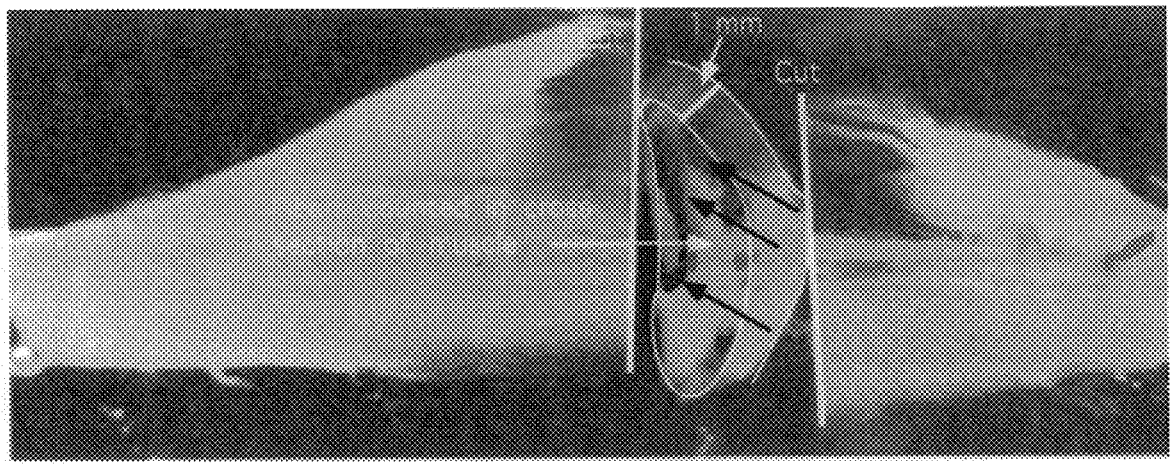
Figure 5:
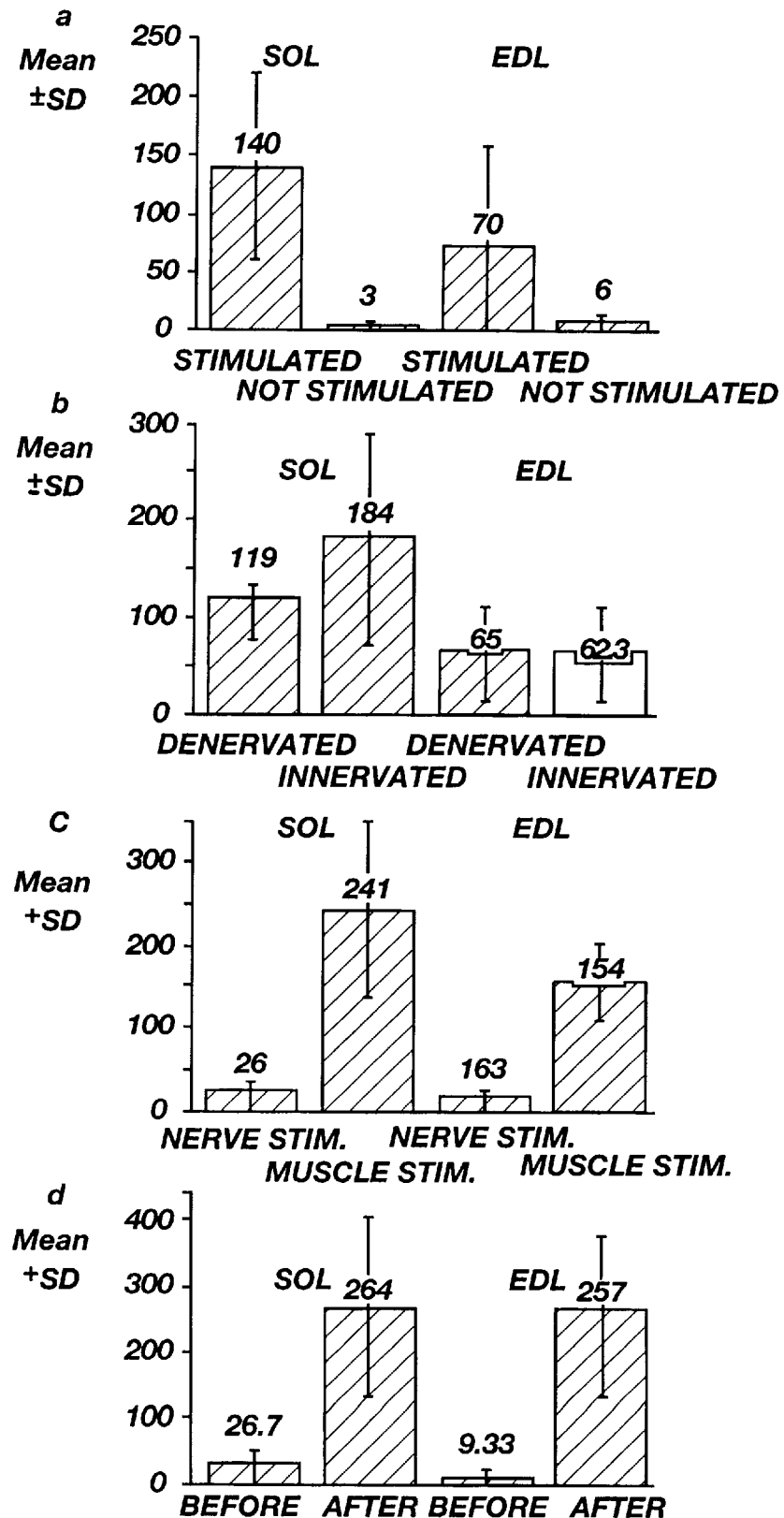

Fifteen days after DNA injection the soleus and EDL muscles were analyzed. As illustrated in FIG. 3a, muscle cells that were stimulated immediately after DNA injection (bottom panels) contain more blue product indicating that more $\beta$-galactosidase gene was introduced into the muscle cells. The transfection efficiency was quantitated by counting the muscle fibers in a 1 mm cross section of the muscle that contained blue product as illustrated in FIG. 4. As illustrated by the bar graph in FIG. 5a, soleus muscle transfected using the method of the present invention showed a 47-fold increase over muscles that were not stimulated. Similarly, EDL muscle transfected using the method of the present invention showed a 12-fold increase over muscles that were not stimulated.

To determine whether nerve activity affected the transfection efficiency, the method of the present invention was performed on innervated (sciatic nerve not transected) and denervated (sciatic nerve transected) soleus and EDL muscles as described above. As illustrated in FIG. 3b, fifteen days after DNA injection both innervated and denervated muscles produced a generous quantity of blue product indicating high efficiency transfer of the $\beta$-galactosidase gene. As illustrated in FIG. 5b, quantitation of transfected muscle fibers confirms high efficiency transfection of both innervated and denervated muscles.

To rule out the possibility that the increased transfection efficiency observed was due to muscle activity, direct stimulation of the sciatic nerve was compared to stimulation of the muscle (n=5). If the increased transfection efficiency was due to muscle activity, the transfection efficiency in muscles stimulated via the nerve should yield similar efficiencies as direct muscle stimulation. As illustrated in FIG. 3c, direct nerve stimulation did not significantly increase transfection efficiencies compared to direct muscle stimulation. As illustrated in FIG. 5c, in both soleus and EDL muscles a 10-fold increase in transfection efficiency was observed with direct muscle stimulation.

As illustrated in FIG. 3d, the increased efficiency is transient, consistent with electroporation. Muscles stimulated directly after DNA injection display significantly more blue dye than muscles that were stimulated prior to DNA injection. In fact, muscles that were stimulated directly after DNA injection displayed transfection efficiencies between 10- and 25-fold greater than muscles that were stimulated 10 minutes prior to DNA injection (FIG. 5d).

Figure 6:
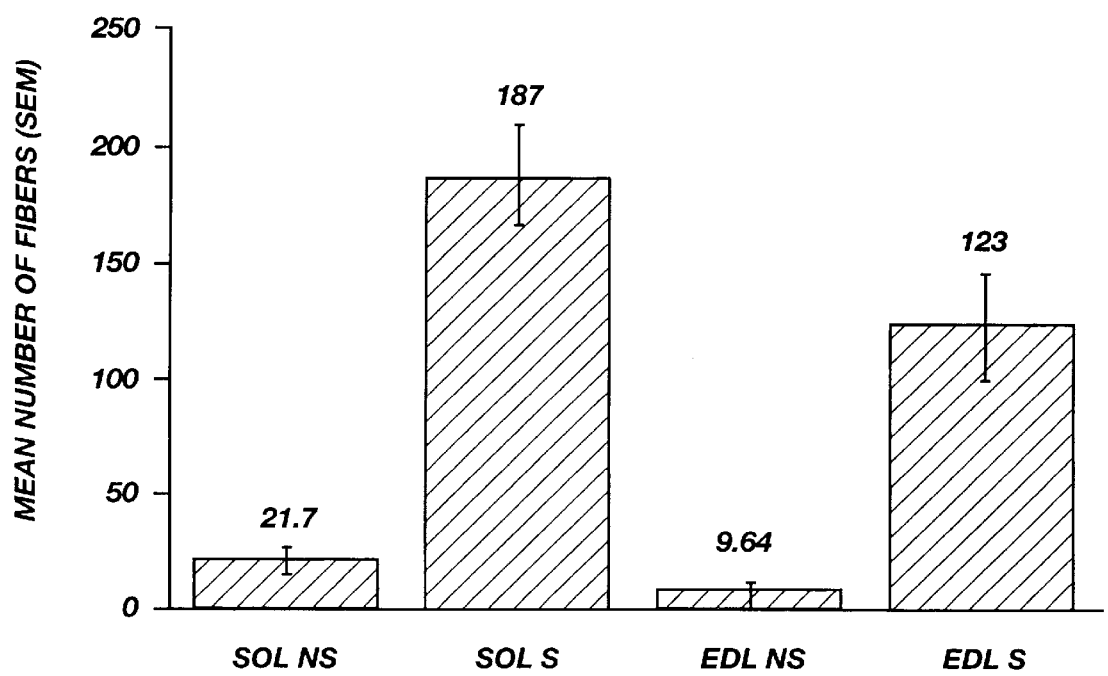
Figure 7:
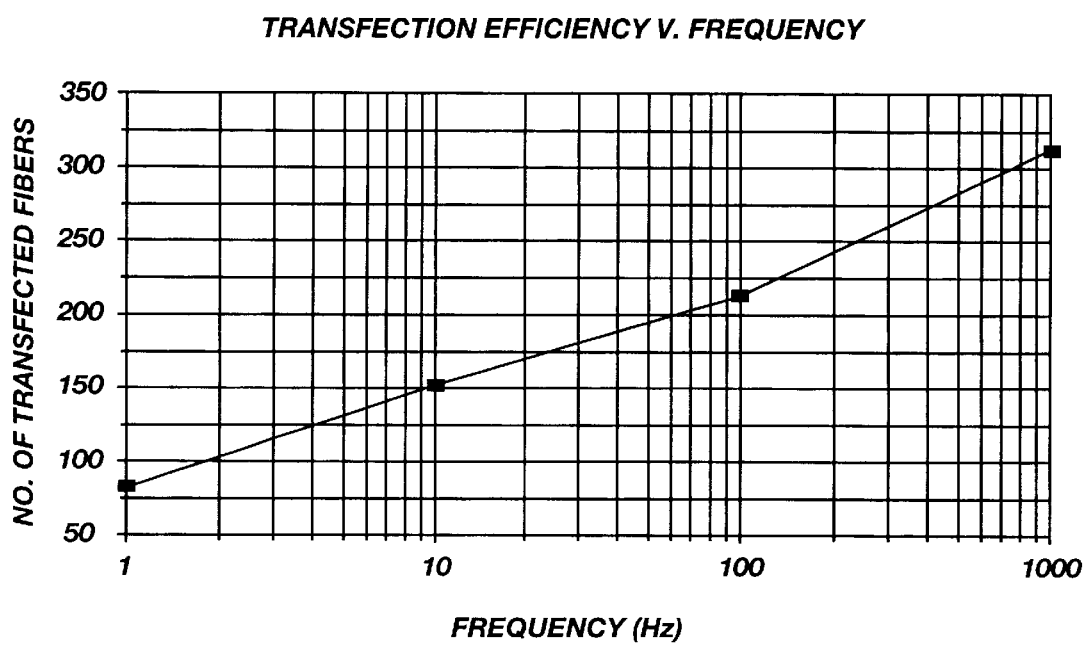
Figure 8:
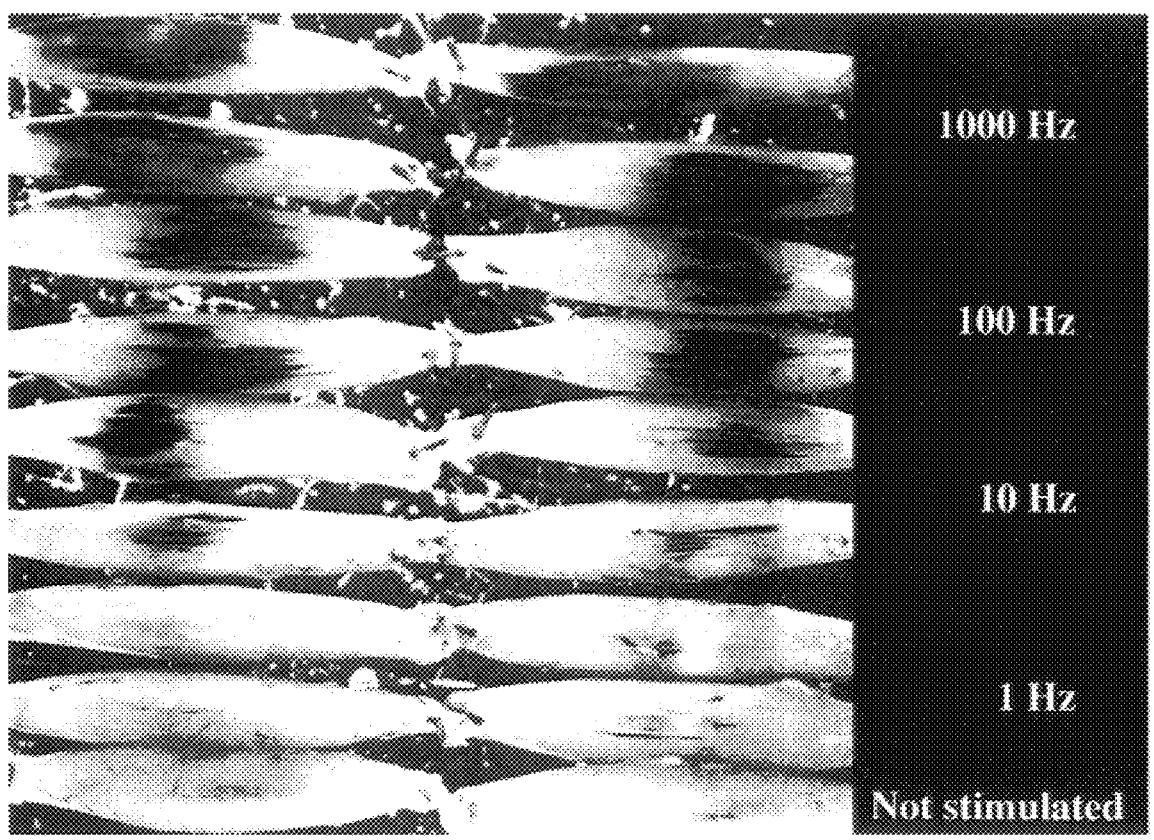

FIG. 6 summarizes the results of the present invention. Muscles from several different experiments and several different batches of DNA are grouped together. In columns marked SOL S and EDL S the muscles (16 in each group) have been stimulated directly after the injection of DNA. In columns marked SOL NS and EDL NS the muscles (10 in each group) have been stimulated by the nerve, not stimulated at all, or stimulated directly 10 minutes before the DNA injection.

The electrical stimulator used for the experiments was manufactured by FHC (Brunswick, Me. 04011). Both Pulsar 6bp and the Pulsar 6bp-a/s stimulators have been used. The Pulsar 6bp-a/s delivers a maximal voltage is 150 V and a maximal current of 50 mA. The maximal voltage that can be delivered requires a resistance between the electrodes of greater than 3000 ohms. The stimulators have been operated at constant voltage mode. Because of the low resistance in the muscle, the voltages have been lower as discussed in the Examples below. In all experiments the current has been maintained at 50 mA.

Figure 9:
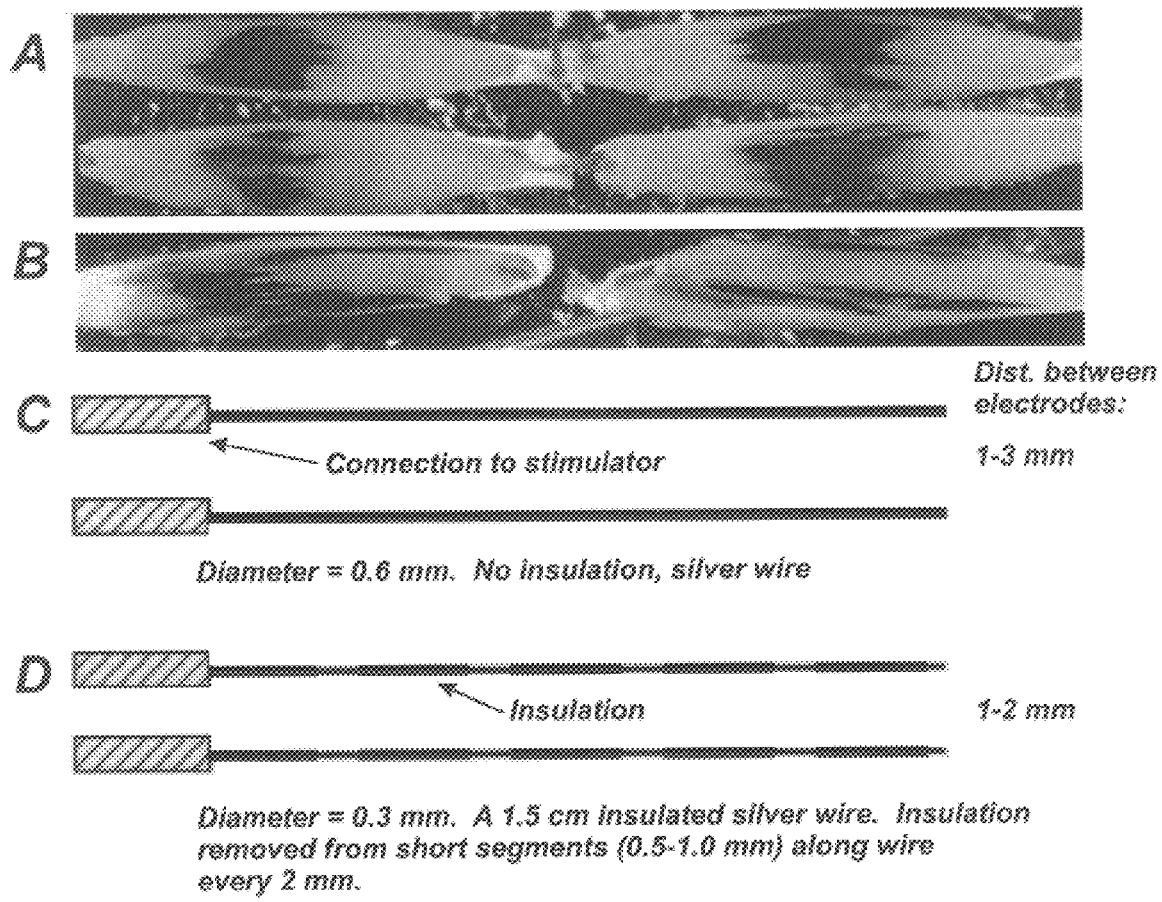

It will be appreciated by one skilled in the art that numerous other electrode configurations can be employed. For example, FIG. 9 illustrates the results obtained using two different electrodes configuration. The electrode shown in (A) was placed perpendicular to the muscle fibers. It consisted of a silver wire with diameter (d) of 0.6 mm, (C) (this is the electrode which was used in all experiments except in (B)). One electrode was placed on each side of the muscle. A short segment in the middle third of the muscle is positive for the Lac Z staining (A), indicating localized expression. In (B) a 1.5 cm electrode made from an insulated silver wire was used (d=0.3 mm). Insulation was removed from short segments (0.5–1.0 mm) along the wire at 2 mm intervals (D). The electrode was penetrated into the muscle in parallel with the muscle fibers. One of the two wires of the electrode was penetrated into the muscle parallel with the muscle fibers. The second wire was placed on the muscle surface, also parallel with the fibers. Both types of electrodes (FIGS. 9c and 9d) gave a similar number of transfected fibers (approximately 250). Using the longer electrode in parallel with the muscle fibers, however, gave a more wide spread staining, indicating a transfection along a longer segment of the fibers and/or increased transfection.

Muscles were stained for Lac Z in whole mounts by methods well known in the art. After staining, the pictures were taken with the bluest side of the muscle up. Thereafter the muscle was cut in three pieces as seen in FIG. 2. The number of blue fibers in about 1 mm thick slice from the middle of the muscle were counted (fibers transfected distally or proximally from the slice are therefore not counted). In order to count the transfected fibers, the slices were dissected into smaller bundles so single fibers could be distinguished under a dissection microscope.

In four (4) muscles the pSV40-luc construct was used. It was injected into the soleus muscle, 3 days after the muscles were removed and luciferase activity was measured using the Promega Luciferase Assay System (Daviset et al., 1993). Uninjected EDL from the same rats were used as control.

It will be appreciated that any nucleic acid can be used with the method of the present invention, for example, plasmid DNA, linear DNA, antisense DNA and RNA. In one preferred embodiment, the nucleic acid is a DNA expression vector of the type well known in the art. Generally, an expression vector contains a promoter operably linked to a DNA molecule that codes for the protein of interest followed by a termination signal such as a polyadenylation signal. Other elements required for bacterial growth and proper mammalian processing may be included, such as the β-lactamase coding region, an f1 origin and ColE1-derived plasmid replication origin. Similar constructs containing a DNA coding region of interest can be constructed by one skilled in the art.

As illustrated in the examples below molecules other than nucleic acids can be delivered to the muscle using the technique of the present invention. In one embodiment, rhodamin conjugated dextran injected into the muscles and stimulated according to the method of the present invention was able to enter muscle cells. In addition, nucleic acid and proteins can be simultaneously introduced into an electroporated muscle. In one embodiment, the large T-antigen nuclear localization signal was mixed with a plasmid containing the DNA coding region for Lac Z. The large T-antigen nuclear localization signal is a protein that binds DNA and facilitates its transport into the nucleus of a cell. In other systems, large T-antigen nuclear localization signal has been shown to increase transfection efficiency. Using the method of the present invention, large T-antigen nuclear localization signal also increased the transfection efficiency of Lac Z indicating that the protein was able to bind the DNA and enter the muscle cell.

7. EXAMPLES

The following examples are given to illustrate various embodiments which have been made of the present invention. It is to be understood that the following examples are not comprehensive or exhaustive of the many types of embodiments which can be prepared in accordance with the present invention.

Example 1

Stimulated Versus Unsimulated Muscles

Transfection efficiencies were determined by injecting skeletal muscles with the pSV40-luc reporter construct into the soleus muscle. Three days after injection, the muscles were removed and luciferase activity was measured using the Promega Luciferase Assay System (Madison, Wis.) according to manufacturer's protocols. Unstimulated EDL muscles from the same rats were used as control. The data are shown below in Table 1.

TABLE 1

STIMULATED VERSUS UNSTIMULATED MUSCLES

| Muscle | Stimulated (Relative luciferase-activity) | Unstimulated (Relative luciferase-activity) | Percent Increase |
|---|---|---|---|
| Soleus animal I | 34.40 | 1.950 | 1664% |
| Soleus animal II | 21.50 | 0.250 | 8500% |
| EDL animal I | | 0.045 | |
| EDL animal II | | 0.046 | |

Example 2

Transfection Efficiency Versus Frequency

Rats were injected with 50 µl of 1 mg/µl of a plasmid carrying lac Z gene. Immediately following injection, electrodes were placed between 2–3 mm apart and the muscle was stimulated with the following stimulation parameters: voltage=30 volts; pulse duration=0.2 ms (total 0.4 ms, bipolar); trains=30, 1 second on 1 second off for 1 minute. Transfected fibers were counted from a 1 mm slice from middle of muscle. The number of transfected fibers is shown below in Table 2 and illustrated in FIG. 7. These data also illustrate that the method of the present invention transfects more than just surface muscle fibers; muscle fibers several cell layers deep are also transfected.

TABLE 2

TRANSEFCTION EFFICIENCY VERSUS FREQUENCY

| Frequency (Hz) | Mean (Transfected Fibers) | Percent Increase with Stimulation |
|---|---|---|
| 0 | 22 | — |
| 1 | 83 | 277% |
| 10 | 153 | 595% |
| 100 | 215 | 877% |
| 1000 | 315 | 1332% |

Example 3

Transfection Efficiency Versus Pulses

Figure 10:
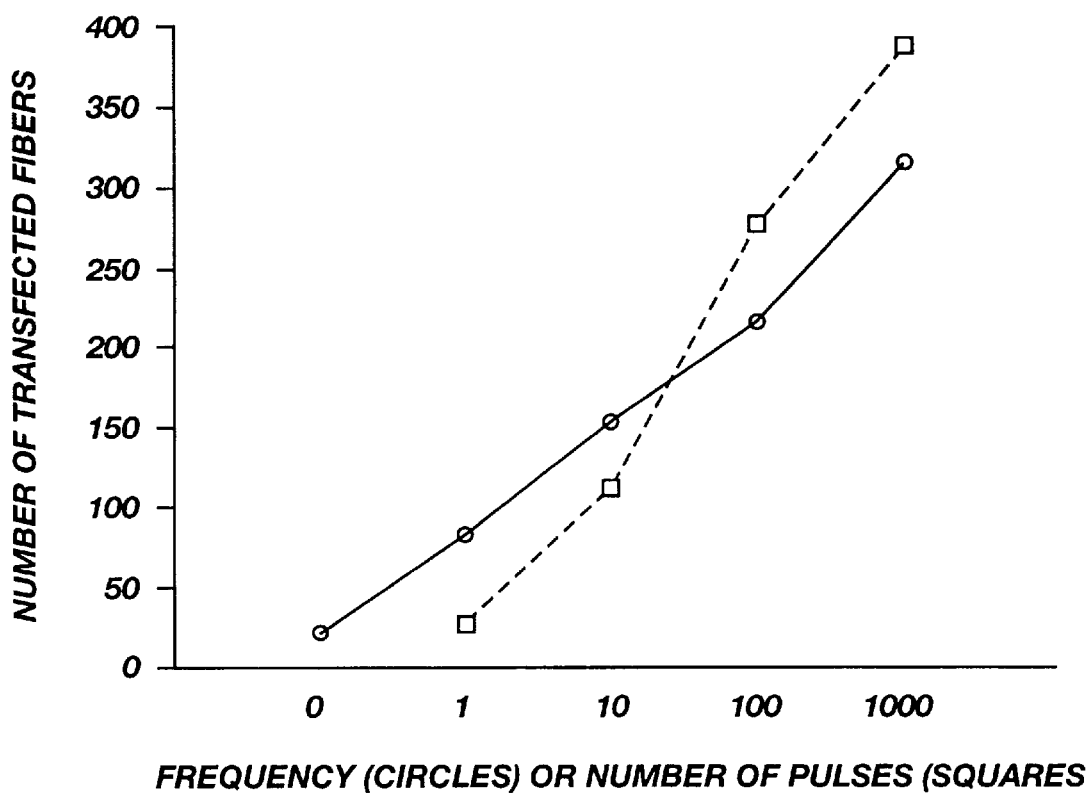
Figure 11:
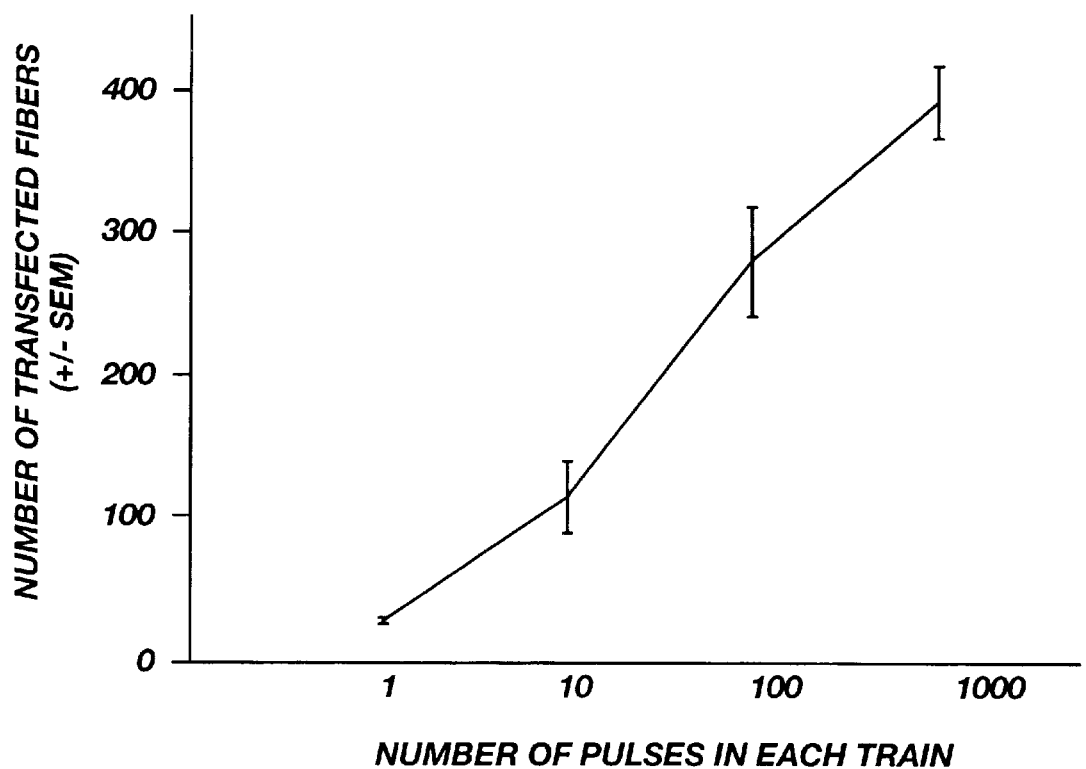
Figure 12:
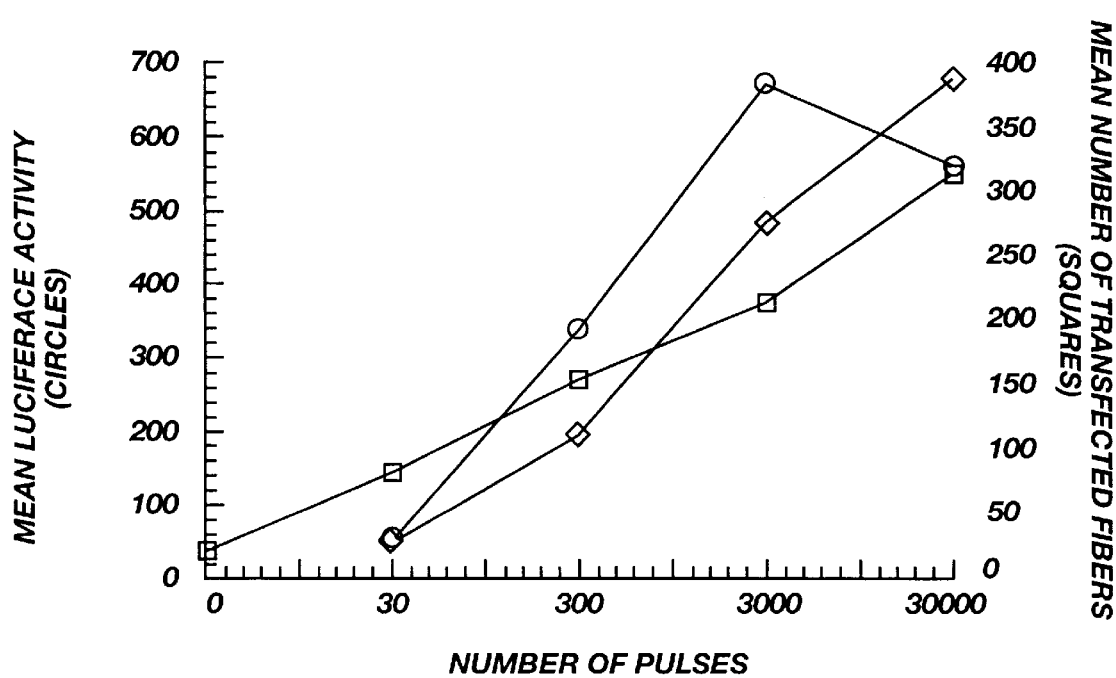

Soleus muscles of Wistar rats (200–270 grams) were injected with 50 µg of RSV luciferase DNA plasmid in 50 µl 0.9% NaCl. Shortly after injection, the muscles were electrically stimulated using the following parameters: 1000 Hz, between 0–1000 bipolar pulses of 200 µl duration in each train were applied to the muscle 30 times over a period of 1 minute. Muscles were removed 3 days after transfection and frozen in liquid nitrogen. Cryostat sections were taken from the of the muscles and stained with Hematoxolin, Eosin and Safran (see Example 9). The remaining pieces were homogenized as described in Example 4 below. As illustrated in FIGS. 10–12, transfection efficiency increased with the number of pulses delivered to the muscle.

Example 4

Determining the Effect of Voltage on Transfection Efficiency

EDL and soleus muscles of Wistar rats (245–263 grams) were injected with 25 µg of RSV driven luciferace plasmid DNA in 50 µl 0.9% NaCl. Shortly after injection, the injected muscles were electrically stimulated using the following parameters: 100 Hz, 100 bipolar pulses in each train of 200 µs duration, voltage varied from between 0 to 47.5. Muscles were removed 4 days post injection and stimulation, homogenized in Promega (Madison, Wis.) luciferace assay buffer and luminescence was measured according to manufacturer's protocols. Macintosh computer and a LabWiev acquisition program were used to capture the first voltage pulses. Recordings were done in parallel with the stimulation electrodes. The voltage measurements were done manually on prints as the average of the maximal voltage of 10 pulses approximately 100 ms after onset of stimulation.

Figure 13A:
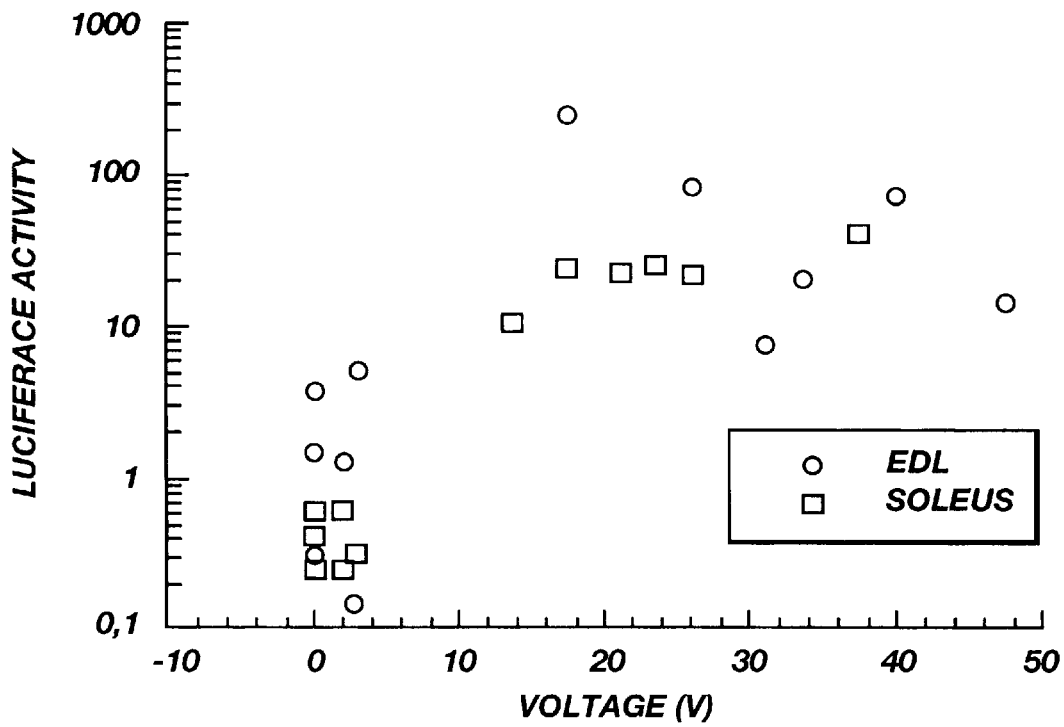
FIG. 13a illustrates the luciferase activity of muscle stimulated with varying volts.
Figure 13B:
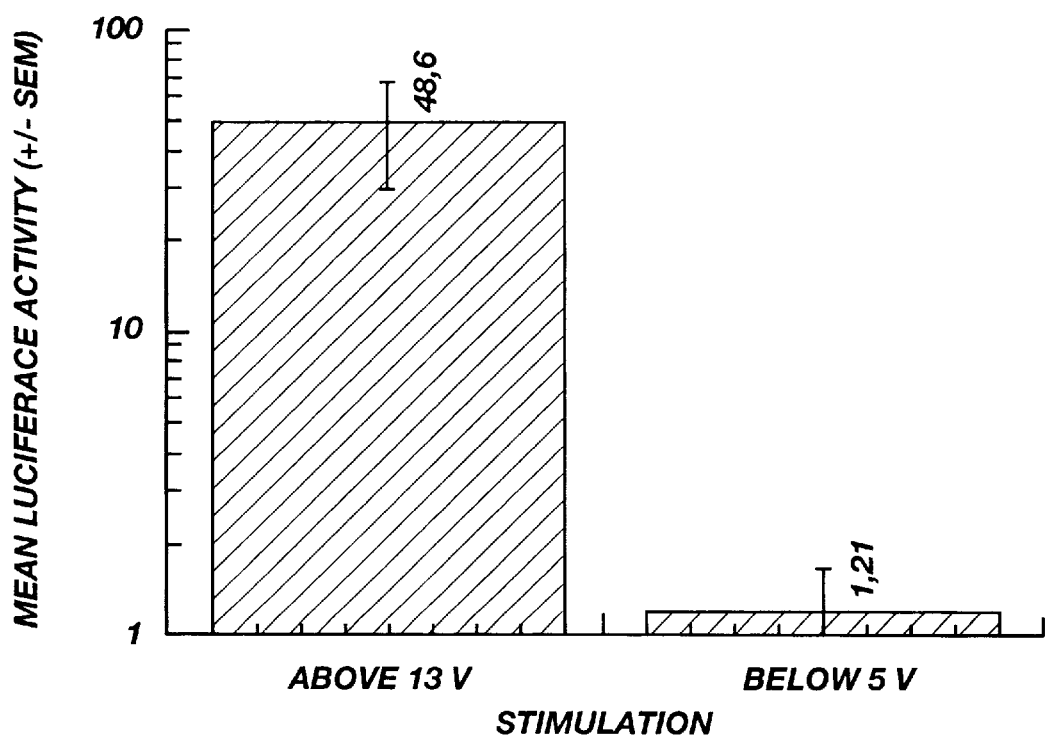
FIG. 13b illustrates the mean luciferace activity of muscles stimulated with an amplitude above 13 volts and below 5 volts.

As illustrated in FIG. 13a, there was a pronounced increase in transfection efficiency with increased voltage. As illustrated in FIG. 13b, under the conditions of this experiment, muscles stimulated with 13 volts or higher showed 40-fold greater luciferace activity compared to muscles stimulated with 5 volts or less.

Example 5

Determining Optimal Pulse Duration

Soleus muscles of Wistar rats (200–270 grams) were injected with 50 µg of DNA plasmid containing the β-galactosidase gene in 50 µl 0.9% NaCl. Shortly after injection, the muscles were electrically stimulated using the following parameters: 100 Hz, 25 volts, 100 bipolar pulses in each train having pulse durations ranging from 5–200 µs. The number of transfected fibers were counted in a 1 mm thick section from the middle of the muscle under a dissection microscope. A second set of rats were injected with 25 µg of RSV-driven luciferace plasmid DNA in 50 µl 0.9% NaCl and electrically stimulated with the same parameters as above except that the pulse durations were varied from 50–2000 µs. As illustrated in Table 3 below and FIG. 14, under these stimulation parameters, the optimal pulse duration ranged from about 50 µs to about 200 µs. This method can be used to optimize the pulse duration of other stimulation parameters.

TABLE 3

TRANSFECTION EFFICIENCY VERSUS PULSE DURATION

| Pulse Duration (µs) | Transfected Fibers (Mean) | Pulse Duration (µs) | Luciferase-activity (Mean) |
|---|---|---|---|
| 0 | — | 0 | 52.7 |
| 5 | 51 | 50 | 631 |
| 20 | 107 | 200 | 536 |
| 50 | 228 | 500 | 348 |
| 200 | 272 | 2000 | 194 |

Example 6

Current Versus Number of Pulses

Soleus muscles of six Wistar rats (178–193 grams) were injected with 50 µg of DNA plasmid containing the β-galactosidase gene in 50 µl 0.9% NaCl. Shortly after injection, the muscles were electrically stimulated as described above except that the pulse duration was varied. The following electroporation parameters were compared: (1) 100 pulses of 50 µs duration versus 1 pulse of 5000 µs; and (2) 10 trains of 100 pulses of 50 µs versus 10 pulses of 5000 µs. Muscles were removed 14 days later and sectioned on a cryostat. Cross sections were stained as previously described. The number of transfected fibers were counted. As illustrated in FIG. 15, longer pulse durations result in higher transfection efficiency.

Example 7

DNA Concentration

EDL muscles of six Wistar rats (178–193 grams) were injected with either 1 µg/µl or 5 µg/µl of DNA plasmid containing the β-galactosidase gene in 50 µl 0.9% NaCl. Shortly after injection, the muscles were electrically stimulated with 30 trains of 100 pulses of 200 µs duration or not stimulated at all. Muscles were removed 14 days later and sectioned on a cryostat. Cross sections were stained as previously described and transfected fibers were counted. As illustrated in FIG. 16, greater transfection efficiencies were obtained with higher DNA concentrates.

Example 8

Large T Antigen Nuclear Localization Signal

Wistar rat muscles were injected with DNA plasmid containing the β-galactosidase gene containing a 100:1 molar excess of large T-antigen nuclear localization signal. This has been shown in other transfection studies to improve the transfection. (See, P. Collas et al. *Transgenic Res.*, 6: 451–8 (1996)). The muscle were stimulated with 10 trains of 100 pulses of 50 µs duration. The muscles containing the large T-antigen nuclear localization signal had the highest number of transfected fibers. Specifically, the muscle co-transfected with large T-antigen nuclear localization signal had 100 and 38 transfected fibers versus 7.3 and 4.7 for the muscles transfected only with DNA, respectively. These data illustrate that transfection efficiencies can be aided by mixing the DNA with non-nucleic acid molecules. In addition, this data illustrates that non-nucleic acid molecules can also be delivered to the muscle using the electroporation techniques of the present invention. No improvement was seen in cells that were not stimulated following injection.

Example 9

Muscle Damage Resulting from Stimulation

Muscles from Example 3 that were sectioned and stained to assess the muscle damage from electroporation. As illustrated in FIG. 17*a*, some damage can occur with injection alone, although the majority of unstimulated muscles were undamaged. In muscles stimulated with 300 pulses, more damage was observed (FIG. 17*b*). As illustrated in FIG. 17*c*, muscle stimulated with 30 trains of 1000 pulses displayed greater damage, indicating that damage is proportional to the extent of stimulation. FIG. 17*d* illustrates that muscles stimulated under the conditions of muscles in 17*c* are completely regenerated and repaired after 14 days.

In another muscle which got the highest amount of stimulation (30 trains of 1000 pulses), plasmid DNA encoding green fluorescent protein (GFP), was also included. FIG. 17*e* illustrates muscles transfected with GFP. Transfected fibers can bee seen in the vicinity of the damaged area (FIG. 17*f*). Transfected regenerating fibers were never observed in cross sections 3 days after electroporation.

Example 10

Genetic Immunization of Rabbits

A female rabbit (4.5 kg) was injected into the right femuralis rectus with 2 milliliters of 1 µg/µl of DNA plasmid containing the rat neural agrin cDNA driven by the CMV promotor (Cohen et al. MCN, 9, 237–53 (1997)). The first milliliter was injected equally in ten places superficial in the muscle followed by 10 trains of 1000 pulses delivered at a frequency of 1000 Hz. The second milliliter was placed further down in the muscle. To test the rabbit serum, rat muscles and COS cells were transfected with the same construct. Muscles were taken out 5 days after transfection and the COS cells were stained 4 days after transfection.

Bleeds were collected at days 0, 19, 50, 81 and 106 and diluted 1:100 and 1:1000. After 19 days the bleed contained enough antibody in the serum to give a weak staining of transfected fibers when diluted 1:10. As a positive control the monoclonal antibody (mAb) AG-86 was used. See Hoch et al. *EMBO J*, 12 (13): 2814–21(1994). Preimmune serum did not show any staining of transfected fibers. Later bleeds all had agrin antibodies in the serum. Bleed collected at day 50 or later contained sufficient antibodies to stained sections at a dilution of 1:1000.

Figure 18A:
Figure 18B:
Figure 18C:
Figure 18D:

FIG. 18*a* illustrates the agrin transfected COS cells stained with antiserum from immunized rabbit (diluted 1:100) and fluorescein conjugated secondary antibody. COS cells were stained first fixing the cells in 1.5% paraformaldehyde for 10 minutes, followed by a 30 minute wash with phosphate buffered saline (PBS). The cells were then blocked with 0.2% bovine serum albumin, triton X-100, 0.1% in PBS 0.1M, for 4 minutes. Serum diluted in same solution was added to the cells and allowed to incubate for 20 minutes. Cells were wash for 4 minutes in PBS and incubated with the secondary antibody (Cappel, 55646) for 10 minutes followed by a PBS wash. Mouse primary mAb Agr-86 was included in the same antibody mixture and rhodamin conjugated secondary antibody (Sigma T-5393, St. Louis. Mo.) was used at a dilution of 1:100. FIG. 18*b* illustrates the same cells stained with mAb Ag-86/rhodamin conjugate. These data illustrate the potential of the technique of the present invention for genetic immunization or DNA vaccine technology.

Example 11

Genetic Immunization of Mice

Groups of two-month old male Sprague Dawley rats were inoculated bilaterally in the EDL and soleus muscles with a total of 200 micrograms (4×50 microliters of a 1 mg/ml solution of DNA in saline) of three different eukaryotic expression vectors containing the cytomegalovirus immediate early promoter (CMV) and the coding sequences for the following proteins: DH-CNTF, an agonistic variant of human ciliary neurotrophic factor (Saggio et al. EMBO J. 14, 3045–3054, 1995); AADH-CNTF, an antagonistic variant of human ciliary neurotrophic factor (Di Marco et al. Proc. Natl. Acad. Sci. U.S.A. 93, 9247–9252, 1996); sec-DHCNTF, a secreted form of DH-CNTF. The muscles were either not electrically stimulated or stimulated immediately after DNA injection using 30 trains of 100 or 1000 square bipolar pulses (duration 200 microseconds; amplitude setting 150 V, effective voltage ~25 V) each, delivered at a frequency of 1000 Hz with a two second interval between successive trains.

Groups of two-month old male CD1 mice were inoculated bilaterally in the quadriceps muscles with 100 micrograms (2×50 microliters of a 1 mg/ml solution of DNA in saline) of sec-DHCNTF plasmid, with or without electrical stimulation of the muscle immediately after DNA injection. Stimulation conditions were 10 trains of 1000 square bipolar pulses (amplitude setting 150 V) delivered at a frequency of 1000 Hz with a two second interval between successive trains.

Blood was collected from the retroorbital sinus at selected time points and serum was prepared and stored at −20° C. The presence of anti-CNTF antibodies in rat and mouse sera was determined by ELISA. Microtiter plates coated with recombinant human CNTF were incubated with serial dilutions of sera, followed by alkaline phosphatase-conjugated antibody against rat or mouse IgG (Pierce). The plates were then incubated in the presence of p-nitrophenyl-phosphate and the absorbance at 405 nm was determined using a microplate reader. Antibody titers were defined as the dilution of serum producing an absorbance reading equal to 50% of that obtained with a saturating concentration of anti-CNTF antiserum.

The results are shown in FIG. 19. Titers could not be averaged with precision, due to the fact that some animals did not develop detectable amounts of antibody. Data are therefore presented for individual animals, with a value of 1:100 representing a low or undetectable antibody titer (reciprocal titer 3/4 100). The results were similar for all plasmids used, as well as for rats and mice, as depicted in FIG. 19. Similar results were also obtained in both rats and mice with another plasmid encoding an unrelated viral protein (data not shown). In both rats and mice, electrical stimulation immediately after DNA injection led to approximately 5 to 10-fold higher antibody titers than simple DNA injection. This was true for stimulation with both high and low numbers of pulses. These results demonstrate that the electroporation method increases the efficiency of DNA-mediated immunization.

Example 12

Secreted Proteins with Systemic Biological Activity

Fifty micrograms (50 microliter of a 1 mg/ml solution in 0.9% NaCl) of a eukaryotic expression plasmid (CMV-EPO) containing the cDNA of mouse erythropoietin under the control of the cytomegalovirus immediate early promoter was injected in the left quadriceps muscle of three-month old 129×Balb/C female mice. In five mice (group 1), the muscles were electrically stimulated immediately after DNA injection using 10 trains of 1000 square bipolar pulses of 200 microseconds duration, with an interval of 2 seconds between successive trains. The frequency of the trains was 1000 Hz and the amplitude set at 150 V (effective voltage ~25 V). In another group of 5 mice (group 2) the muscles were not stimulated after DNA injection. As a control, a group of 4 mice (group 3) was injected with a plasmid (CMV-GFP) containing the coding sequence for green fluorescence protein under the control of the CMV promoter, followed by electrical stimulation at the same conditions as group 1. Group 4 consisted of 5 mice injected only with saline solution without electrical stimulation.

Blood was collected from the retroorbital sinus at selected time points and hematocrit was measured by centrifugation in capillary tubes. Serum samples were analyzed for the presence of EPO using a commercial ELISA kit (R&D Systems). The results are shown in Table 4. In all groups of mice, except those that were injected with the EPO construct and electrically stimulated immediately thereafter, circulating EPO levels were below the limit of detection of the ELISA kit (<15 mU/ml). In contrast, mice injected with the EPO construct and electrically stimulated had significantly elevated serum EPO levels 5 days after injection (average of approximately 50 mU/ml). The serum concentration of EPO remained elevated for up to 28 days following DNA injection (latest time point examined; data not shown). These levels of EPO produced an increase in hematocrits, which rose from 46.2% prior to injection to 70.0% and 76.7% at 14 and 28 days after DNA injection, respectively. These values were significantly different from those obtained with both control groups (groups 3 and 4) and from those of mice injected with the EPO expression vector without electrical stimulation of the muscle (group 2). Indeed, the latter had hematocrit levels not significantly different from those of the control groups (see Table 4). These results demonstrate that the electroporation method is superior to simple DNA injection both in terms of the expression levels of a secreted protein and in producing a biological effect mediated by the secreted protein.

TABLE 4

EPO Serum Concentrations and Activity

| | | Day 2 | | Day 5 | | Day 14 | |
| --- | --- | --- | --- | --- | --- | --- | --- |
| | Mouse No. | HCT % | mEPO (mU/ml) | HCT % | mEPO (mU/ml) | HCT % | mEPO (mU/ml) |
| Group 1 CMV-EPO Stimulated | 7 | 45 | ND | ND | 55.7 | 71 | 72.4 |
| | 8 | 48 | ND | ND | 54.6 | 68 | 5.3 |
| | 9 | 47 | ND | ND | 59 | 75.5 | 48.7 |
| | 10 | 44 | ND | ND | 62.2 | 69.5 | 62.9 |
| | 11 | 47 | ND | ND | 7.9 | 66 | 22.4 |
| | Avg. | 46.2 | ND | ND | 47.9 | 70.0[abc] | 48.3 |
| | Stand. Dev. | 1.6 | | | | 3.6 | |
| Group 2 CMV-EPO No stimulation | 12 | 45 | ND | ND | ND | 50 | <15 |
| | 13 | 45 | ND | ND | ND | 50 | <15 |
| | 14 | ND | ND | ND | ND | 48 | <15 |
| | 15 | 46 | ND | ND | ND | 49.5 | <15 |
| | 16 | 44 | ND | ND | ND | 52 | <15 |
| | Avg. | 45 | ND | ND | ND | 49.9 | <15 |
| | Stand. Dev. | 0.8 | | | | | |

TABLE 4-continued

EPO Serum Concentrations and Activity

| | | Day 2 | | Day 5 | | Day 14 | |
|---|---|---|---|---|---|---|---|
| | Mouse No. | HCT % | mEPO (mU/ml) | HCT % | mEPO (mU/ml) | HCT % | mEPO (mU/ml) |
| Group 3 CMV-GFP Stimulated | 2 | ND | ND | ND | <15 | 43.5 | <15 |
| | 3 | ND | ND | ND | <15 | 48 | <15 |
| | 5 | ND | ND | ND | <15 | 46 | <15 |
| | 6 | ND | ND | ND | <15 | 46 | <15 |
| | Avg. | ND | ND | ND | <15 | 45.9 | <15 |
| | Stand. Dev. | | | | | 1.8 | |
| Group 4 CMV-EPO | 17 | 45 | ND | ND | <15 | 45.5 | ND |
| | 18 | 45 | ND | ND | <15 | 49 | ND |
| | 19 | 43 | ND | ND | <15 | 48 | ND |
| | 20 | 45 | ND | ND | <15 | 51.5 | ND |
| | 21 | 50 | ND | ND | <15 | 47 | ND |
| | Avg. | 45.6 | ND | ND | <15 | 48.2 | ND |
| | Stand. Dev. | 2.6 | | | | 2.3 | |

ND = not determined.
[a] $p < 0.0001$ vs. group 2;
[b] $p < 0.0001$ vs. group 3;
[c] $p < 0.0001$ vs. group 4 (Fisher's protected least significant difference).

Example 13

Delivery on Non-nucleic Acid Molecules

Muscles were injected with 50 µl of a mixture of GPF plasmid DNA 1 µg/µl and 2 µg/µl rhodamin-conjugated dextran (10 kD from Molecular Probes). Three to 5 days later the muscles (n=6) were frozen in liquid nitrogen and sectioned on a cryostat. As illustrated in FIG. 20, stimulated muscles (bottom) were transfected with rhodamin-conjugated dextran (top) and GFP (middle). As further illustrated, the same muscle fibers were transfected with both GFP and rhodamin-conjugated dextran. These data indicate that non-nucleic acid molecules can be delivered to muscle cells using the technique of the present invention.

We claim:

1. A method of delivering a molecule to the skeletal muscle of a mammal in vivo comprising:

injecting a molecule into a skeletal muscle of the mammal;

positioning electrodes near the injection site such that current traveling through the electrodes passes through the injection site; and electrically stimulating the muscle with an electrical current having a field strength in the range of from about 25 V/cm to less than 200 V/cm.

2. The method of delivering a molecule of claim 1 wherein said electrical stimulation is delivered in the form of a single square bipolar pulse.

3. The method of delivering a molecule of claim 2 wherein said bipolar pulse has a duration of between about 50 µs and 5000 µs.

4. The method of delivering a molecule of claim 1 wherein said electrical stimulation is delivered in the form of between about 2 to 30,000 square bipolar pulses.

5. The method of delivering a molecule of claim 4 wherein said bipolar pulses have a total duration of between about 10 ms to 12,000 ms.

6. The method of delivering a molecule of claim 5 wherein said bipolar pulses are delivered in the form of at least two trains.

7. The method of delivering a molecule of claim 6 wherein the frequency of said electrical stimulation is between about 0.5 Hz and 1000 Hz.

8. The method of delivering a molecule of claim 1 wherein said molecule is a nucleic acid, said nucleic acid operably linked to a promoter which directs the expression in said muscle cells of the protein coded by said nucleic acid.

9. A method of genetically immunizing a mammal by transfecting a nucleic acid into the skeletal muscle of said mammal in vivo comprising:

injecting a skeletal muscle of the mammal with a nucleic acid operably linked to a promoter which directs the expression in said muscle of the protein coded by said nucleic acid;

positioning electrodes near said nucleic acid injection site such that current traveling through the electrodes passes through said nucleic acid injection site; and stimulating the muscle with an electrical current having a field strength in the range of from about 5 V/cm to less than 200 V/cm.

10. The method of delivering a molecule of claim 9 wherein said electrical stimulation is delivered in the form of a single square bipolar pulse.

11. The method of delivering a molecule of claim 10 wherein said bipolar pulse has a duration of between about 50 µs and 5000 µs.

12. The method of delivering a molecule of claim 9 wherein said electrical stimulation is delivered in the form of between about 2 to 30,000 square bipolar pulses.

13. The method of delivering a molecule of claim 12 wherein the sum of the pulse durations of said bipolar pulses is between about 10 ms to 12,000 ms.

14. The method of delivering a molecule of claim 13 wherein said bipolar pulses are delivered in the form of at least two trains.

15. The method of delivering a molecule of claim 14 wherein the frequency of said electrical stimulation is between about 0.5 Hz and 1000 Hz.

16. A method of systemically delivering a protein to a mammal comprising:

injecting a muscle of the mammal with a nucleic acid operably linked to a promoter which directs the expression in said muscle of the protein coded by said nucleic acid;

positioning electrodes near said nucleic acid injection site such that current traveling through the electrodes passes through said nucleic acid injection site; and stimulating the muscle with an electrical current having a field strength in the range of from about 5 V/cm to less than 200 V/cm.

17. The method of delivering a molecule of claim 16 wherein said electrical stimulation is delivered in the form of a single square bipolar pulse.

18. The method of delivering a molecule of claim 17 wherein said bipolar pulse has a duration of between about 50 µs and 5000 µs.

19. The method of delivering a molecule of claim 18 wherein said electrical stimulation is delivered in the form of between about 2 to 30,000 square bipolar pulses.

20. The method of delivering a molecule of claim 19 wherein the sum of the pulse durations of said bipolar pulses is between about 10 ms to 12,000 ms.

21. The method of delivering a molecule of claim 20 wherein said bipolar pulses are delivered in the form of at least two trains.

22. The method of delivering a molecule of claim 21 wherein the frequency of said electrical stimulation is between about 0.5 Hz and 1000 Hz.

* * * * *